US006858222B2

(12) United States Patent
Nelson et al.

(10) Patent No.: US 6,858,222 B2
(45) Date of Patent: Feb. 22, 2005

(54) FABRICATION OF DRUG LOADED BIODEGRADABLE POLYMER FIBERS

(75) Inventors: Kevin D Nelson, Arlington, TX (US); Andres A. Romero-Sanchez, Arlington, TX (US); George M. Smith, Lexington, KY (US); Nadir Alikacem, Allen, TX (US); Delia Radulescu, Arlington, TX (US); Paula Waggoner, Burleson, TX (US); Zhibing Hu, Denton, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/428,354

(22) Filed: May 2, 2003

(65) Prior Publication Data

US 2003/0203003 A1 Oct. 30, 2003

Related U.S. Application Data

(62) Division of application No. 09/632,457, filed on Aug. 4, 2000, now Pat. No. 6,596,296.
(60) Provisional application No. 60/147,827, filed on Aug. 6, 1999.

(51) Int. Cl.$^7$ .............................. A61F 2/02; A61K 47/30
(52) U.S. Cl. ..................................... 424/426; 514/772.3
(58) Field of Search ........................ 424/426; 514/772.3

(56) References Cited

U.S. PATENT DOCUMENTS

| | | | |
|---|---|---|---|
| 4,464,321 A | 8/1984 | Pittalis et al. | 264/83 |
| 4,965,128 A | 10/1990 | Greidanus et al. | 428/398 |
| 5,166,187 A | 11/1992 | Collombel et al. | 514/21 |
| 5,263,984 A | 11/1993 | Li et al. | 623/15 |
| 5,270,300 A | 12/1993 | Hunziker | 514/12 |
| 5,290,271 A | 3/1994 | Jernberg | 604/891.1 |
| 5,342,348 A | 8/1994 | Kaplan | 605/891.1 |
| 5,567,612 A | 10/1996 | Vacanti et al. | 435/240.23 |
| 6,596,296 B1 * | 7/2003 | Nelson et al. | 424/426 |

FOREIGN PATENT DOCUMENTS

| | | |
|---|---|---|
| EP | 0 328 050 A2 | 8/1989 |
| WO | WO 98/20190 | 5/1998 |
| WO | WO 00/47716 | 8/2000 |

OTHER PUBLICATIONS

Aigner et al., "Cartilage tissue engineering with novel nonwoven structured biomaterial based on hyaluronic acid benzyl ester," *J. of Biomed. Materials Res.,* 42(2):172–81, 1998.
Auerbeach and Auerbach, "Angiogenesis inhibition: a review," *Pharmac. Ther.,* 63:265, 1994.
Breitbart et al., "Tissue engineered bone repair of calvarial defects using cultured periosteal cells," *Plastic & Reconstructive Surgery,* 101(3):567–74, 1998.
Cao et al., "Comparative study of the use of poly(glycolic acid), calcium alginate and pluronics in the engineering of autologous porcine cartilage," *J. of Biomaterials Sci., Polymer Edition,* 9(5):475–87, 1998.
Dillon et al., "The influence of physical structure and charge on neurite extension in a 3D hydrogel scaffold," *J. of Biomaterials Sci., Polymer Ed.,* 9(10):1049–69, 1998.
Elcin et al., "Xenotransplantation of fetal porcine hepatocytes in rats using a tissue engineering approach," *Artificial Organs,* 23(2):146–52, 1999.

(List continued on next page.)

*Primary Examiner*—Carlos A. Azpuru
(74) *Attorney, Agent, or Firm*—Jenkens & Gilchrist, P.C.

(57) ABSTRACT

The invention provides tissue engineering compositions and methods wherein three-dimensional matrices for growing cells are prepared for in vitro and in vivo use. The matrices comprise biodegradable polymer fibers capable of the controlled delivery of therapeutic agents. The spatial and temporal distribution of released therapeutic agents is controlled by use of defined nonhomogeneous patterns of therapeutic agents in the matrices.

23 Claims, 11 Drawing Sheets

OTHER PUBLICATIONS

Fidler and Ellis, "The implications of angiogenesis for the biology and therapy of cancer metastasis," *Cell,* 79:185, 1994.

Folkman and Klagsbrun, "Angiogenic factors," *Science,* 235:442–447, 1987.

Folkman, "How is blood vessel growth regulated in normal and neoplastic tissue," *Cancer Res.,* 46:467, 1986.

Folkman, J., "Angiogenesis in cancer, vascular, rheumatoid and other disease," *Nature Med.,* 1:27, 1995.

Grande et al., "Evaluation of matrix scaffolds for tissue engineering of articular cartilage grafts," *J. of Biomed. Mat. Res.,* 34(2):211–20, 1997.

Gutsche et al., "Engineering of a sugar–derivatized porous network for hepatocyte culture," *Biomaterials,* 17(3):387–93, 1996.

Hoerstrup et al., "Tissue engineering: a new approach in cardiovascular surgery–seeding of human fibroblasts on resorbable mesh," *Swiss Surgery,* (Suppl.), 2:23–5, 1998.

Hoerstrup et al., "Fluorescence activated cell sorting: a reliable method in tissue engineering of a bioprosthetic heart valve," *Annals of Thoracic Surgery,* 665(5):1653–7, 1998.

Isogai et al., "Formation of phalanges and small joints by tissue–engineering," *J. of Bone & Joint Surgery, American vol.,* 81(3):306–16, 1999.

Martin et al., "In vitro differentation of chick embryo bone marrow stromal cells into cartilaginous and bone–like tissues," *J. of Orthopaedic Res.,* 16(2):181–9, 1998.

Nagy et al., "Pathogenesis of ascites tumor growth: vascular permeability factor, vascular hyperpermeability, and ascites fluid accumulation," *Cancer Res.,* 55:360, 1995.

Peppas and Langer, "New challenges in biomaterials," *Science,* 263:1715–1720, 1994.

Peter et al., "Polymer concepts in tissue engineering," *J. of Biomed. Materials Res.,* 43(4):422–7, 1998.

Sacks et al., "Collagen fiber architecture of a cultured dermal tissue," *J. of Biomed. Engineering,* 119(1):124–7, 1997.

Shinoka et al., "Creation of viable pulmonary artery autografts through tissue engineering," *J. of Thoracic & Cardiovascular Surgery,* 115(3):536–45, 1998.

Sims et al., "Tissue engineered neocartilage using plasma derived polymer substrates and chondrocytes," *Plastic & Reconstructive Surgery,* 101(6):1580–5, 1998.

Vunjak–Novakovic et al. "Dynamic cell seeding of polymer scaffolds for cartilage tissue engineering," *Biotechnology Progress,* 14(2):193–202, 1998.

Whang et al., "Ectopic bone formation via rhBMP–2 delivery from porous bioabsorbably polymer scaffolds," *J. of Biomed. Materials Res.,* 42(4):491–9, 1998.

Wong and Mooney, "Synthesis and properties of biodegradable polymers used in tissue engineering," *In: Synthetic Biodegradable Polymer Scaffolds,* (Atala and Mooney, eds.), Birkhauser Press, Boston, MA, pp. 51–82, 1997.

Yoo and Atala, "A novel gene delivery system using urothelial tissue engineered neoorgans," *J. of Urology,* 158(3 Pt 2):1066–70, 1997.

Fauza et al., "Videofetoscopically assisted fetal tissue engineering: skin replacement," *J. of Pediatric Surgery,* 33(2):357–61, 1998.

* cited by examiner

FABRICATION OF DRUG LOADED BIODEGRADABLE POLYMER FIBERS

This application is a divisional of application Ser. No. 09/632,457, filed Aug. 4, 2000, now U.S. Pat. No. 6,596,296 which claims the benefit of U.S. Provisional Application No. 60/147,827, filed Aug. 6,1999.

BACKGROUND OF THE INVENTION

1. Field of the Invention

This invention relates to the field of medicine and tissue engineering, and in particular to drug releasing biodegradable implants.

2. Description of Related Art

Tissue engineering is a discipline wherein living cells are used to replace functional loss because of injury, disease, or birth defect in an animal or human. These replacement cells can be autologous, allogenic, or, in limited circumstances, xenogenic. The field of tissue engineering is a new area of medicine and optimal procedures have yet to be elucidated.

At present, there are several primary avenues investigators are using to engineer tissues. One is to harvest cells from a healthy donor, preferably from the same individual, or at least from an appropriate donor of the same species, and grow those cells on a scaffold in vitro. This scaffold is typically a three-dimensional polymer network, often composed of biodegradable fibers. Cells adherent to the polymer network can then typically be induced to multiply. This cell filled scaffold can be implanted into the impaired host with the goal that the cells will perform their physiological function and avoid destruction by the host immune system. To this end, it is important that purified cell lines are used, as the introduction of non-self immune cells can up-regulate a strong host immune attack. The difficulty with this approach is the scaffolding must be small, as no cell can survive more than a couple millimeters away from a source of oxygen and nutrients. Therefore, large scaffolds cannot be used, as the scaffold will not vascularize adequately in time to save the cells in the interior regions.

In another approach, an empty three-dimensional, biodegradable polymer scaffold is directly implanted in the patient, with the goal of inducing the correct type of cells from the host's body to migrate into the polymer scaffold. The benefit is that vascularization can happen simultaneously with migration of cells into the matrix. A major problem is that there is currently no way to ensure that the appropriate cell types will migrate into the scaffold, and that the mechanical and biological properties will be maintained to provide the patient's physiological need.

In both of the above approaches, the scaffold may be biodegradable, meaning that over time it will break down both chemically and mechanically. As this break down occurs, the cells secrete their own extracellular matrix, which plays a critical role in cell survival and function. In normal tissue, there is an active and dynamic reciprocal exchange between the constitutive cells of the tissue and the surrounding extracellular matrix. The extracellular matrix provides chemical signals that regulate the morphological properties and phenotypic traits of cells and may induce division, differentiation or even cell death. In addition, the cells are also constantly rearranging the extracellular matrix. Cells both degrade and rebuild the extracellular matrix and secrete chemicals into the matrix to be used later by themselves or other cells that may migrate into the area. It has also been discovered that the extracellular matrix is one of the most important components in embryological development. Pioneering cells secrete chemical signals that help following cells differentiate into the appropriate final phenotype. For example, such chemical signals cause the differentiation of neural crest cells into axons, smooth muscle cells or neurons.

The integrated relationship between extracellular matrix and tissue cells establishes the extracellular matrix as an important parameter in tissue engineering. If cells are desired to behave in a specific manner, then the extracellular matrix must provide the appropriate environment and appropriate chemical/biological signals to induce that behavior for that cell type. Currently it is not possible to faithfully reproduce a biologically active extracellular matrix. Consequently, some investigators use a biodegradable matrix that enables the cells to create their own extracellular matrix as the exogenous matrix degrades.

In the above-described approaches to tissue engineering, a polymer scaffolding provides not only the mechanical support, but also the three-dimensional shape that is desired for the new tissue or organ. Because cells must be close to a source of oxygen and nutrients in order to survive and function, a major current limitation is that of blood supply. Most current methodologies provide no specific means of actively assisting the incorporation of blood vessels into and throughout the polymer matrix. This places limitations on the physical size and shape of the polymer matrix. The only current tissue-engineering device that has made it into widespread clinical use is artificial skin, which by definition is of limited thickness. The present invention provides compositions and methods that promote the directed migration of appropriate cell types into the engineered extracellular matrix. By directing specific three-dimensional cell migration and functional patterns, directed vascularization can be induced, which overcomes the current limitations on the shape and size of polymer implants. It also ensures that appropriate cell types will be physically located in specific locations within the matrix. Compositions and methods are provided to modulate phenotypic expression as a function of both time and space.

SUMMARY OF THE INVENTION

The present invention provides tissue engineering compositions and methods wherein three-dimensional matrices for growing cells are prepared for in vitro and in vivo use. The matrices comprise biodegradable polymer fibers capable of the controlled delivery of therapeutic agents. The spatial and temporal distribution of released therapeutic agents is controlled by the use of predefined nonhomogeneous patterns of polymer fibers, which are capable of releasing one or more therapeutic agents as a function of time. The terms "scaffold," "scaffold matrix" and "fiber-scaffold" are also used herein to describe the three dimensional matrices of the invention. "Defined nonhomogeneous pattern" in the context of the current application means the incorporation of specific fibers into a scaffold matrix such that a desired three-dimensional distribution of one or more therapeutic agents within the scaffold matrix is achieved. The distribution of therapeutic agents within the matrix fibers controls the subsequent spatial distribution within the interstitial medium of the matrix following release of the agents from the polymer fibers. In this way, the spatial contours of desired concentration gradients can be created within the three dimensional matrix structure and in the immediate surroundings of the matrix. Temporal distribution is controlled by the polymer composition of the fiber and by the use of coaxial layers within a fiber.

One aspect of the present invention is a biocompatible implant composition comprising a scaffold of biodegradable polymer fibers. In various embodiments of the present invention, the distance between the fibers may be about 50 microns, about 70 microns, about 90 microns, about 100 microns, about 120 microns, about 140 microns, about 160 microns, about 180 microns, about 200 microns, about 220 microns, about 240 microns, about 260 microns, about 280 microns, about 300 microns, about 320 microns, about 340 microns, about 360 microns, about 380 microns, about 400 microns, about 450 microns or about 500 microns. In various embodiments the distance between the fibers may be less than 50 microns or greater than 500 microns.

Additionally, it is envisioned that in various embodiments of the invention, the fibers will have a diameter of about 20 microns, about 40 microns, about 60 microns, about 80 microns, about 100 microns, about 120 microns, about 140 microns, about 160 microns, about 180 microns, about 200 microns, about 220 microns, about 240 microns, about 260 microns, about 280 microns, about 300 microns, about 320 microns, about 340 microns, about 360 microns, about 380 microns, about 400 microns, about 450 microns or about 500 microns (including intermediate lengths). In various embodiments the diameter of the fibers may be less than about 20 microns or greater than about 500 microns. Preferably, the diameter of the fibers will be from about 60 microns to about 80 microns.

"About", in this one context is intended to mean a range of from 1–10 microns, which includes the intermediate lengths within the range. It will be readily understood that "intermediate lengths", in this context, means any length between the quoted ranges, such as 21, 22, 23, 24, 25, 26, 27, 28, 29 etc.; 30, 31, 32, etc.; 50, 51, 52, 53, etc.; 100, 101, 102, 103, etc.; 150, 151, 152, 153, etc.; including all integers through the 200–500 range.

The inventors also contemplate that the matrix may be woven, non-woven, braided, knitted, or a combination of two or more such preparations. For example, potential applications such as artificial arteries may well use a combination of woven, non-woven and knitted preparations or a combination of all four preparations. In certain embodiments of the invention, braided compositions may find particular utility for use with tendons and ligaments. Such braiding may, for example, provide superior strength.

In certain embodiments of the invention, the fibers containing one or more therapeutic agents are distributed within the scaffold matrix in a defined nonhomogeneous pattern. In one embodiment, the fibers may comprise two or more subsets of fibers that differ in biodegradable polymer content. The fibers or subsets of fibers may comprise a plurality of co-axial biodegradable polymer layers.

In another embodiment of the present invention, the fibers or a subset of fibers, contain one or more therapeutic agents such that the concentration of the therapeutic agent or agents varies along the longitudinal axis of the fibers or subset of fibers. The concentration of the active agent or agents may vary linearly, exponentially or in any desired fashion, as a function of distance along the longitudinal axis of a fiber. The variation may be monodirectional, that is, the content of one or more therapeutic agents decreases from the first end of the fibers or subset of the fibers to the second end of the fibers or subset of the fibers. The content may also vary in a bidirection fashion, that is, the content of the therapeutic agent or agents increases from the first ends of the fibers or subset of the fibers to a maximum and then decreases towards the second ends of the fibers or subset of the fibers.

In certain embodiments of the present invention, a subset of fibers comprising the scaffold may contain no therapeutic agent. For fibers that contain one or more therapeutic agents, the agent or agents may include a growth factor, an immunodulator, a compound that promotes angiogenesis, a compound that inhibits angiogenesis, an anti-inflammatory compound, an antibiotic, a cytokine, an anti-coagulation agent, a procoagulation agent, a chemotactic agent, an agents that promotes apoptosis, an agent that inhibits apoptosis, a mitogenic agent, a radioactive agent, a contrast agent for imaging studies, a viral vector, a polynucleotide, therapeutic genes, DNA, RNA, a polypeptide, a glycosaminoglycan, a carbohydrate, a glycoprotein. The therapeutic agents may also include those drugs that are to be administered for long-term maintenance to patients such as cardiovascular drugs, including blood pressure, pacing, anti-arrhythmia, beta-blocking drugs, and calcium channel based drugs. Therapeutic agents of the present invention also include anti-tremor and other drugs for epilepsy or other movement disorders. These agents may also include long term medications such as contraceptives and fertility drugs. They could comprise neurologic agents such as dopamine and related drugs as well as psychological or other behavioral drugs. The therapeutic agents may also include chemical scavengers such as chelators, and antioxidants. Wherein the therapeutic agent promotes angiogenesis, that agent may be vascular endothelial growth factor. The therapeutic agents may be synthetic or natural drugs, proteins, DNA, RNA, or cells (genetically altered or not). As used in the specification and claims, following long-standing patent law practice, the terms "a" and "an," when used in conjunction with the word "comprising" or "including" means one or more.

In general, the present invention contemplates the use of any drug incorporated in the biodegradable polymer fibers of the invention. The word "drug" as used herein is defined as a chemical capable of administration to an organism, which modifies or alters the organism's physiology. More preferably the word "drug" as used herein is defined as any substance intended for use in the treatment or prevention of disease. Drug includes synthetic and naturally occurring toxins and bioaffecting substances as well as recognized pharmaceuticals, such as those listed in "The Physicians Desk Reference," 471st edition, pages 101–321; "Goodman and Gilman's The Pharmacological Basis of Therapeutics" 8th Edition (1990), pages 84–1614 and 1655–1715; and "The United States Pharmacopeia, The National Formulary", USP XXII NF XVII (1990), the compounds of these references being herein incorporated by reference. The term "drug" also includes compounds that have the indicated properties that are not yet discovered or available in the U.S. The term "drug" includes pro-active, activated, and metabolized forms of drugs.

The biodegradable polymer may be a single polymer or a co-polymer or blend of polymers and may comprise poly (L-lactic acid), poly(DL-lactic acid), polycaprolactone, poly (glycolic acid), polyanhydride, chitosan, or sulfonated chitosan, or natural polymers or polypeptides, such as reconstituted collagen or spider silk.

One aspect of the present invention is a drug-delivery fiber composition comprising a biodegradable polymer fiber containing one or more therapeutic agents. In one embodiment, the content of the one or more therapeutic agents within the fiber varies along the longitudinal axis of the fiber such that the content of the therapeutic agent or agents decreases from the first end of the fiber to the second end of the fiber. In another embodiment, the fiber comprises a plurality of co-axial layers of biodegradable polymers. The drug delivery fiber composition may be implanted into many sites in the body including dermal tissues, cardiac tissue, soft tissues, nerves, bones, and the eye. Ocular implantation has particular use for treatment of cataracts, diabetically induced proliferative retinopathy and non-proliferative retinopathy, glaucoma, macular degeneration, and pigmentosa XXXX.

Another aspect of the present invention is a method of controlling the spatial and temporal concentration of one or more therapeutic agents within a fiber-scaffold implant, comprising implanting a fiber-scaffold into a host. The spatial concentrations may be provided across multiple fibers, or alternatively along a single fiber by imposing a concentration gradient along the length of a fiber. The fiber-scaffold typically comprises biodegradable polymer fibers containing one or more therapeutic agents, wherein the therapeutic agent or agents are distributed in the fiber-scaffold in a defined nonhomogeneous pattern. The host will typically be an animal, preferably a mammal and more preferably a human.

Yet another aspect of the present invention is a method of producing a fiber-scaffold for preparing an implant capable of controlling the spatial and temporal concentration of one or more therapeutic agents. This method generally comprises forming biodegradable polymer fibers into a three dimensional fiber-scaffold. The biodegradable polymer fibers contain one or more therapeutic agents. The therapeutic agent or agents are distributed in the fiber-scaffold in a defined nonhomogeneous pattern.

It is further envisioned that the scaffold of the invention may be used to direct and/or organize tissue structure, cell migration and matrix deposition and participate in or promote general wound healing.

In another embodiment of the invention, a method is provided for creating a drug releasing fiber from chitosan comprising use of hydrochloric acid as a solvent and Tris base as a coagulating bath. The hydrochloric acid concentration may be, for example, from about 0.25% to about 5%, or from about 1% to about 2%, including all concentrations within such ranges. In the method, the tris base concentration may be, for example, from about 2% to about 25%, from about 4% to about 17%, or from about 5% to about 15%, including all concentrations within such ranges. The method may, in one embodiment of the invention, comprise a heterogeneous mixture comprising chitosans with different degrees of deacetylation. The method may also comprise creating a drug releasing fiber comprising segments of chitosan with different degrees of deacetylation.

A drug releasing fiber in accordance with the invention may be created, for example, from chitosan and extracellular matrix. In creating a drug releasing fiber in accordance with the invention, the chitosan concentration may be, for example, from about 0.5 wt. % to about 10 wt. %, from about 1 wt. % to about 7 wt. %, from about 2 wt. % to about 5 wt. %, from about 3 wt. % to about 4 wt. %, or about 3.5 wt. %. In one embodiment of the invention, the Matrigel. The extracellular matrix concentration may be from about 1 vol. % to about 20 vol. %, from about 2 vol. % to about 15 vol. %, from about 3 vol. % to about 10 vol. %, or from about 4 vol. % to about 6 vol. %, including about 5 vol. %. In the method, the fiber may be coated with said extracellular matrix.

Chitosan used in accordance with the invention may be sulfated or unsulfated. In one embodiment of the invention, when sulfated chitosan is used the concentration may be from about 0.025 wt. % to about 2 wt. %, from about 0.05 wt. % to about 1 wt. %, from about 0.1 wt. % to about 0.5 wt. %, or from about 0.15 wt. % to about 0.3 wt. %, including about 0.2 wt. %. In the method, chitosan and sulfated chitosan may be extruded into a fiber.

In still another embodiment of the invention, a method is provided of creating a drug releasing fiber, the method comprising adding poly(L-lactic acid) microspheres to chitosan in acid and a coagulation bath. In the method, the acid may be, for example, acetic acid or hydrochloric acid. Where the acid is hydrochloric acid, the concentration may be, for example, from about 0.25% to about 5%, or from about 1% to about 2%, including 1.2 vol. % and all other concentrations within such ranges. The chitosan concentration may be, for example, from about 0.5 wt. % to about 10 wt. %, from about 1 wt. % to about 7 wt. %, from about 2 wt. % to about 5 wt. %, from about 3 wt. % to about 4 wt. %, or about 3.5 wt. %. The coagulation bath may comprise sodium hydroxide, for example, in a concentration of about 1 vol. % to about 20 vol. %, 2 vol. % to about 15 vol. %, 3 vol. % to about 10 vol. %, 4 vol. % to about 7 vol. %, or about 4 vol. % to about 6 vol. %, including about 5 vol. %. In one embodiment of the invention, the method comprises adding poly(L-lactic acid) microspheres to a solution of about 3.5 wt. % chitosan in from about 1 vol. % hydrochloric acid to about 2 vol. % hydrochloric acid and using a coagulation bath comprising from about 5 vol. % tris base to about 15 vol. % tris base. The method may further comprise adding a surfactant to the solution, including albumin, for example, from about 1 wt. % to about 5 wt. % of said albumin, including about 3 wt. %. In yet another embodiment of the invention, a composition of chitosan fibers is provided comprising microspheres of a second polymer, said microspheres comprising one or more biological molecules. The composition may comprise a surfactant that is a biological molecule.

In yet another embodiment of the invention, a composition is provided comprising a fiber containing chitosan and an extracellular matrix. The chitosan may be sulfated or non-sulfated.

In yet another embodiment of the invention, a composition is provided comprising a three-dimensional scaffold, said scaffold comprising fibers that are woven, non-woven, or knitted, wherein said fibers comprise any of the compositions described herein above. A composition in accordance with the invention may, in one embodiment, comprise fibers containing chitosan, extracellular matrix and a biological molecule. The chitosan may sulfated non-sulfated.

In yet another embodiment of the invention, a composition is provided comprising a heterogeneous scaffold of fibers a biological molecule as described above, wherein the biological molecule not the same for all fibers of the scaffold. In the composition, the degree of deacetylation may vary as a function of distance along the fiber. The composition may an extracellular matrix. The composition may also, in certain embodiments of the invention, comprise sulfated or non-sulfated chitosan.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A illustrates that a single polymer fiber can maintain the lumen of any tubular body, such as arteries, veins, or ducts. FIG. 3B illustrates that multiple polymer fibers can maintain the lumen of tubular bodies. The numerals 21–22 denote fibers loaded with therapeutic agents.

FIG. 4 shows that a fiber may have multiple component coatings, with each component loaded with different therapeutic agents. The numerals 11–13 denote therapeutic agents.

FIG. 6 illustrates a fiber containing a linear gradient of therapeutic agent along its length top) and graphically illustrates the linear gradient (bottom).

FIG. 9A graphically illustrates changes in the ultimate strength [Mpa] when the ratio of winding speed to the infusion speed is varied. Results shown are for polymers having 10-wt %, 8-wt %, and 7.5-wt %. FIG. 9B graphically illustrates changes in percent elongation with varying ratios of winding velocity (Vw) to infusion velocity (Vi).

FIG. 10A graphically illustrates changes in ultimate strength with polymer concentration (wt %) when the winding speed to infusion speed ratio (Vw/Vi) is 26.82 and 23.49. FIG. 10B illustrates changes in elasticity with polymer weight percent for the same ratios.

FIG. 11A shows a fiber having a smooth surface texture. FIG. 11B shows a fiber having a veloured surface texture. FIG. 11C shows a fiber having a longitudinally grooved surface texture.

DESCRIPTION OF ILLUSTRATIVE EMBODIMENTS

The present invention provides compositions and methods to create a heterogeneous, woven, knitted, or non-woven or braided three-dimensional matrix for growing cells in tissue engineering applications. These scaffolds can be used in vitro and in vivo, and due to their heterogeneity can create both spatial and temporal distributions of therapeutic agents. In this invention, therapeutic agents may include drugs, proteins, peptides, mono- and di-saccharides, polysaccharides, glycoproteins, DNA, RNA, viruses, or other biological molecules of interest. The term therapeutic agent in this invention also includes radioactive materials used to help destroy harmful tissues such as tumors in the local area, or to inhibit growth of healthy tissues, such as in current stent applications; or markers to be used in imaging studies.

A. Three Dimensional Fiber Matrix

To create the heterogeneous scaffolds of the present invention, the therapeutic agents are encapsulated into individual fibers of the matrix by methods to be described herein. The therapeutic agents are released from each individual fiber slowly, and in a controlled manner. The fiber format has many advantages as a drug delivery platform over other slow drug-releasing agents known to those familiar in the art such as microspheres, porous plugs or patches. The primary advantage of fibers is that they can provide complex three-dimensional woven (FIG. 1), or non-woven (FIG. 2) scaffolding, with or without patterning, to allow cells to attach, spread, differentiate, and mature into appropriately functioning cells. Because they can form patterns, a "smart fabric" can be woven to induce cells of specific types to migrate to specific regions of the scaffold due to specific chemotactic factors being released. This scaffold mimics the function of the extracellular matrix material both during embryological development and in post-embryological tissues. Additionally, filaments could be formed into a unique scaffold that provides a growth substrate for tissue repair or reconstruction that is not reminiscent of a natural like structure.

Because of the ability to weave patterns to induce appropriate cell types into specific regions, it is possible to incorporate strands that will induce the formation of blood vessels into the fabric. This may be accomplished by providing fibers that release growth factors such as vascular endothelial growth factor (VEGF). By appropriate spacing of VEGF containing-fibers into the weave pattern, large tissues may be engineered, and the cells in such tissues can be provided with a sufficient blood supply and thereby receive oxygen and nutrients and enable the removal of waste products.

Figure 3A:
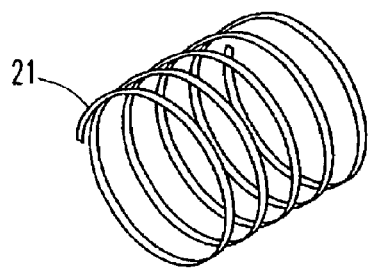
FIG. 3A and FIG. 3B: Fibers can provide the body with short term mechanical support in such applications as stents.
Figure 3B:
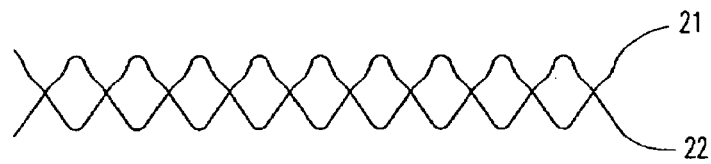

Fibers also have the advantage of providing the body with short term mechanical support in such applications as stents (FIGS. 3A and 3B), wherein the polymer fiber can maintain the lumen of any tubular body, such as arteries, veins, ducts (e.g. bile duct, ureter, urethra, trachea, etc.), organs of the digestive track such as esophagus, intestine, colon, and connective tissue such as tendons, ligaments, muscle and bone. The fibers provide a useful structure to support mechanical strength or tension during the healing process. Fibers may also be useful to promote neural regeneration or reconstruction of nerves or spinal cord.

Figure 4:
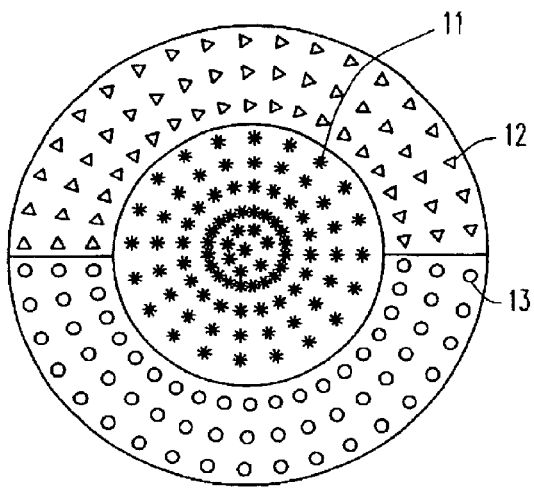
FIG. 4: Fibers can be coated to form co-axial fibers.
Figure 5:
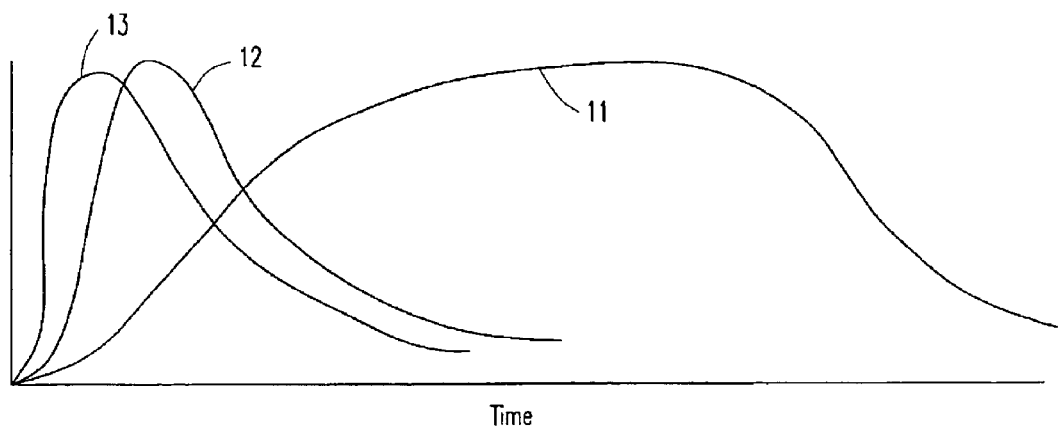
FIG. 5: Shows the release kinetics of a coated fiber, as shown in FIG. 4, having a two component coating with each component loaded with different therapeutic agents. The numerals 11–13 denote therapeutic agents.

Further, fibers can be coated, forming co-axial fibers as shown in FIG. 4. Each coating can be of a different polymer material, or combination of polymers, and each layer can release a different therapeutic agent or combination of therapeutic agents. The coating can also be physically divided into multiple sections, meaning that if desired, different therapeutic agents can be released in various directions. For example, as depicted in FIG. 4, a fiber may have a two component coating, with each component loaded with different therapeutic agents. Therefore, not only is spatial distribution of various therapeutic agents possible, as described above, but these agents may have different release kinetics, thus yielding temporal distribution of therapeutic agents. The release kinetics of such a coated fiber is characterized in FIG. 5. For example, if a fiber has two coatings over the core polymer, then three different therapeutic agents or combinations of therapeutic agents can be released. The outside coating will release its therapeutic agents followed by the inner coating material and finally from the core fiber. Therefore, each polymer system has its own release kinetics profile that can be adjusted by polymer type and processing conditions for that particular coating layer. Each coating can consist of different polymers as well as being loaded with different molecules. This provides the ability to control release kinetics at each layer. The ability to release different agents at different times is particularly important in tissue engineering, because cells that are rapidly dividing often do not display the specialized functions of non-dividing cells of the same type of class. With the present invention, it is possible, by release of the appropriate therapeutic agents, to induce cells to first migrate to a specific location, then enter a rapid division phase to fill the tissue space, and then differentiate into a functional form.

Figure 6:
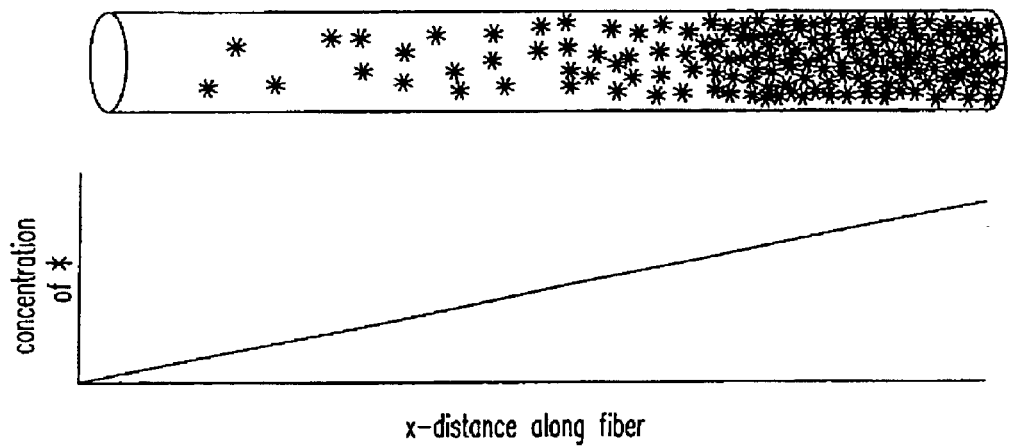
FIG. 6: Fibers may contain linear gradients of therapeutic agents along their length.
Figure 7:
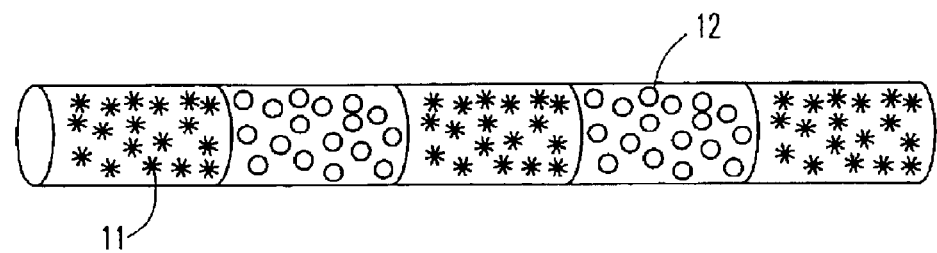
FIG. 7: Shows a banded fiber having more than one therapeutic agent with possibly varying concentrations along its length. The distribution and frequency of the bands can be changed as desired. The numerals 11 –12 denote therapeutic agents.

Additionally, cells are known to follow concentration gradients. It is the change in concentration of a particular factor that appears to be important for directed cell migration. Therefore, the present invention provides a method of achieving gradients of therapeutic agents along the length of the fibers. A linear gradient is depicted in FIGS. 6A and 6B. By methods disclosed in this invention, this concentration gradient can be linear, exponential, or any other shape as a function of distance along the length of the fiber. It can also be bi-directional, meaning that it can be low at both ends and reach a maximum in the middle for example. This induces the cells to migrate and grow in specific directions along the fibers. By extension, by methods disclosed in this invention, a banded fiber can also be produced, as shown in FIG. 7. The distribution and frequency of these bands can be changed as desired. Therefore, the therapeutic agents delivery aspect of this invention goes far beyond simple drug-delivery microspheres or plugs, and the fiber based "smart scaffold" exceeds typical fiber based matrices into orchestrating the development of viable tissue, providing a three-dimensional biological, architecture as well as mechanical support.

B. Biodegradable Polymers

Preferred polymers for use in the present invention include single polymer, co-polymer or a blend of polymers of poly(L-lactic acid), poly(DL-lactic acid), polycaprolactone, poly(glycolic acid), polyanhydride, chitosan, or sulfonated chitosan. Naturally occurring polymers may also be used such as reconstituted collagen or natural silks. Those of skill in the art will understand that these polymers are just examples of a class of biodegradable polymer matrices that may be used in this invention. Further biodegradable matrices include polyanhydrides, polyorthoesters, and poly(amino acids) (Peppas and Langer, 1994). Any such matrix may be utilized to fabricate a biodegradable polymer matrix with controlled properties for use in this invention. Further biodegradable polymers that produce non-toxic degradation products are listed in Table 1.

TABLE 1

Main Polymers Recognized as Biodegradable

Synthetic

Polypeptides
    Polydepsipeptides
    Nylon-2/nylon-6 copolyamides
    Aliphatic polyesters
        Poly(glycolic acid) (PGA) and copolymers
        Poly(lactic acid) (PLA) and copolymer
        Poly(alkylene succinates)
        Poly(hydroxy butyrate) (PHB)
        Poly(butylene diglycolate)
        Poly($\epsilon$-caprolactone) and copolymers
    Polydihydropyrans
    Polyphosphazenes
    Poly(ortho ester)
    Poly(cyano acrylates)

Natural

Modified polysaccharides
        cellulose, starch, chitin
    Modified proteins
        collagen, fibrin Adapted from Wong and Mooney, 1997.

C. Agents that Promote Angiogenesis

One class of therapeutic agents to be encapsulated by the polymer fibers of the present invention are therapeutic agents that promote angiogenesis. The successful engineering of new tissue requires the establishment of a vascular network. The induction of angiogenesis is mediated by a variety of factors, any of which may be used in conjunction with the present invention (Folkman and Klagsbrun, 1987, and references cited therein, each incorporated herein in their entirety by reference). Examples of angiogenic factors includes, but is not limited to: vascular endothelial growth factor (VEGF) or vascular permeability factor (VPF); members of the fibroblast growth factor family, including acidic fibroblast growth factor (aFGF) and basic fibroblast growth factor (bFGF); interleukin-8 (IL-8); epidermal growth factor (EGF); platelet-derived growth factor (PDGF) or platelet-derived endothelial cell growth factor (PD-ECGF); transforming growth factors alpha and beta (TGF-$\alpha$, TGF-$\beta$); tumor necrosis factor alpha (TNF-$\alpha$); hepatocyte growth factor (HGF); granulocyte-macrophage colony stimulating factor (GM-CSF); insulin growth factor-1 (IGF-1); angiogenin,; angiotropin; fibrin and nicotinamide (Folkman, 1986, 1995; Auerbach and Auerbach, 1994; Fidler and Ellis, 1994; Folkman and Klagsbrun, 1987; Nagy et al., 1995)

D. Cytokines

In certain embodiments the use of particular cytokines incorporated in the polymer fibers of the present invention is contemplated. Table 2 below is an exemplary, but not limiting, list of cytokines and related factors contemplated for use in the present invention.

TABLE 2

| Cytokine | Reference |
|---|---|
| Human IL-1 | March et al., Nature, 315:641, 1985 |
| Murine IL-1 | Lomedico et al., Nature, 3 12:458, 1984 |
| Human IL-1 | March et al., Nature, 315:641, 1985; Auron et al., Proc. Natl. Acad. Sci. USA, 81:7907, 1984 |
| Murine IL-1 | Gray, J. Immunol., 137:3644, 1986; Telford, NAR, 14:9955, 1986 |
| Human IL-1ra | Eisenberg et al., Nature, 343:341, 1990 |
| Human IL-2 | Taniguchi et al., Nature, 302:305, 1983; Maeda et al., Biochem. Biophys. Res. Commun., 115:1040, 1983 |
| Human IL-2 | Taniguchi et al., Nature, 302:305, 1983 |
| Human IL-3 | Yang et al., Cell, 47:3, 1986 |
| Murine IL-3 | Yokota et al., Proc. Natl. Acad. Sci. USA, 81:1070, 1984; Feng et al., Nature, 307:233, 1984; Miyatake |
| et al., Proc. Natl. Acad. Sci. U.S.A.,82:316, 1985 | |
| Human IL-4 | Yokota et al., Proc. Natl. Acad. Sci. USA, 83:5894, 1986 |
| Murine IL-4 | Norma et al., Nature, 319:640, 1986; Lee et al., Proc. Natl. Acad. Sci. USA, 83:2061, 1986 |
| Human IL-5 | Azuma et al., Nuc. Acids Res., 14:9149, 1986 |
| Murine IL-5 | Kinashi et al., Nature, 324:70, 1986; Mizuta et al., Growth Factors, 1:51, 1988 |
| Human IL-6 | Hirano et al., Nature, 324:73, 1986 |
| Murine IL-6 | Van Snick et al., Eur. J. Immunol., 18:193, 1988 |
| Human IL-7 | Goodwin et al., Proc. Natl. A cad. Sci. USA, 86:302, 1989 |
| Murine IL-7 | Namen et al., Nature, 333:571, 1988 |
| Human IL-8 | Schmid et al., J. Immunol., 139:250, 1987; Matsushima et al., J. Exp. Med., 167:1883, 1988; Lindley et al., Proc. Natl. Acad. Sci. USA, 85:9199, 1988 |
| Human IL-9 | Renauld et al., J. Immunol., 144:4235, 1990 |
| Murine IL-9 | Renauld et al., J. Immunol., 144:4235, 1990 |
| Human Angiogenin | Kurachi et al., Biochemistry, 24:5494, 1985 |
| Human GRO | Richmond et al., EMBO J., 7:2025, 1988 |
| Murine MIP-1 | Davatelis et al., J. Exp. Med., 167:1939, 1988 |
| Murine MIP-1 | Sherry et al., J. Exp. Med., 168:225 1, 1988 |
| Human MIF | Weiser et al., Proc. Natl. Acad. Sci. USA, 86:7522, 1989 |
| Human G-CSF | Nagata et al., Nature, 319:415, 1986; Souza et al., Science, 232:61, 1986 |
| Human GM-CSF | Cantrell et al., Proc. Natl. Acad. Sci. USA, 82:6250, 1985; Lee et al., Proc. Natl. Acad. Sci. USA, 82:4360, 1985; Wong et al., Science, 228:810, 1985 |
| Murine GM-CSF | Gough et al., EMBO J., 4:645, 1985 |
| Human M-CSF | Wong, Science, 235:1504, 1987; Kawasaki, Science, 230;291, 1985; Ladner, EMBO J., 6:2693, 1987 |
| Human EGF | Smith et al., Nuc. Acids Res., 10:4467, 1982; Bell et al., NAR, 14:8427, 1986 |
| Human TGF- | Derynck et al., Cell, 38:287, 1984 |
| Human FGF acidic | Jaye et al., Science, 233:541, 1986; Gimenez-Gallego et al., Biochem. Biophys. Res. Commun., 138:611, 1986; Harper et al., Biochem., 25:4097, 1986 |
| Human -ECGF | Jaye et al., Science, 233:541, 1986 |
| Human FGF basic | Abraham et al., EMBO J., 5:2523, 1986; Sommer et al., Biochem. Biophys. Res. Comm., 144:543, 1987 |
| Murine IFN- | Higashi et al., J. Biol. Chem., 258:9522, 1983; Kuga, NAR, 17:3291, 1989 |
| Human IFN- | Gray et al., Nature, 295:503, 1982; Devos et al., NAR, 10:2487, 1982; Rinderknecht, J. Biol. Chem., 259:6790, 1984 |
| Human IGF-I | Jansen et al., Nature, 306:609, 1983; Rotwein et al., J. Biol. Chem., 261:4828, 1986 |
| Human IGF-II | Bell et al., Nature, 310:775, 1984 |
| Human -NGF chain | Ullrich et al., Nature, 303:821, 1983 |
| Human NT-3 | Huang EJ. Et al., Development. 126(10):2191-203, 1999 May. |
| Human PDGF A chain | Betsholtz et al., Nature, 320:695, 1986 |
| Human PDGF B chain | Johnsson et al., EMBO J., 3:921, 1984; Collins et al., Nature, 316:748, 1985 |
| Human TGF-1 | Derynck et al., Nature, 316:701, 1985 |
| Human TNF- | Pennica et al., Nature, 312:724, 1984; Fransen et al., Nuc. Acids Res., 13:4417, 1985 |
| Human TNF- | Gray et al., Nature, 312:721, 1984 |
| Murine TNF- | Gray et al., Nucl. Acids Res., 15:3937, 1987 |
| Human E-Selectin | Bevilacqua et al., Science, 243:1160, 1989; Hensley et al., J. Biol. Chem., 269:23949, 1994 |
| Human ICAM-1 | Simmons et al., Nature, 331:624, 1988 |
| Human PECAM | Simmons et al., J Exp. Med., 171:2147, 1990 |
| Human VCAM-1 | Hession et al., J. Biol. Chem., 266:6682; Osborn et al., Cell, 59: 1203, 1989 |
| Human L-Selectin | Ord et al., J. Biol. Chem., 265:7760, 1990; Tedder et al., |

TABLE 2-continued

| Cytokine | Reference |
| --- | --- |
| (membrane bound) | J. Exp. Med., 170:123, 1989 |
| Human L-Selectin (soluble form) | Ord et al., J. Biol. Chem., 265:7760, 1990; Tedder et al., J. Exp. Med., 170:123, 1989 |
| Human Calcitonin | Le Moullec et al., FEBS Lett., 167:93, 1984 |
| Human Hirudin (E. coli optimized) | Dodt et al., FEBS Lett., 165:180, 1984 |

E. Polynucelotides

The polynucleotides to be incorporated within the polymer fibers of the present invention, extend to the full variety of nucleic acid molecules. The nucleic acids thus include genomic DNA, cDNAs, single stranded DNA, double stranded DNA, triple stranded DNA, oligonucleotides, Z-DNA, mRNA, tRNA and other RNAs. DNA molecules are generally preferred, even where the DNA is used to express a therapeutic RNA, such as a ribozyme or antisense RNA.

A "gene" or DNA segment encoding a selected protein or RNA, generally refers to a DNA segment that contains sequences encoding the selected protein or RNA, but is isolated away from, or purified free from, total genomic DNA of the species from which the DNA is obtained. Included within the terms "gene" and "DNA segment", are DNA segments and smaller fragments of such segments, and also recombinant vectors, including, for example, plasmids, cosmids, phage, retroviruses, adenoviruses, and the like.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, such as sequences encoding leader peptides or targeting sequences, later added to the segment by the hand of man.

The present invention does not require that highly purified DNA or vectors be used, so long as any coding segment employed encodes a selected protein or RNA and does not include any coding or regulatory sequences that would have a significant adverse effect on the target cells. Therefore, it will also be understood that useful nucleic acid sequences may include additional residues, such as additional non-coding sequences flanking either of the 5' or 3' portions of the coding region or may include various internal sequences, i.e., introns, that are known to occur within genes.

Many suitable DNA segments may be obtained from existing, including commercial sources. One may also obtain a new DNA segment encoding a protein of interest using any one or more of a variety of molecular biological techniques generally known to those skilled in the art. For example, cDNA or genomic libraries may be screened using primers or probes with designed sequences. Polymerase chain reaction (PCR) may also be used to generate a DNA fragment encoding a protein of interest.

After identifying an appropriate selected gene or DNA molecule, it may be inserted into any one of the many vectors currently known in the art, so that it will direct the expression and production of the selected protein when incorporated into a target cell. In a recombinant expression vector, the coding portion of the DNA segment is positioned under the control of a promoter/enhancer element. The promoter may be in the form of the promoter that is naturally associated with a selected gene, as may be obtained by isolating the 5' non-coding sequences located upstream of the coding segment or exon, for example, using recombinant cloning and/or PCR technology.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a selected gene in its natural environment. Such promoters may include those normally associated with other selected genes, and/or promoters isolated from any other bacterial, viral, eukaryotic, or mammalian cell. Naturally, it will be important to employ a promoter that effectively directs the expression of the DNA segment in the chosen target cells.

The use of recombinant promoters to achieve protein expression is generally known to those of skill in the art of molecular biology, for example, see Sambrook et al. (1989; incorporated herein by reference). The promoters employed may be constitutive, or inducible, and can be used under the appropriate conditions to direct high level or regulated expression of the introduced DNA segment. Expression of genes under the control of constitutive promoters does not require the presence of a specific substrate to induce gene expression and will occur under all conditions of cell growth. In contrast, expression of genes controlled by inducible promoters is responsive to the presence or absence of an inducing agent.

Promoters isolated from the genome of viruses that grow in mammalian cells, e.g., RSV, vaccinia virus 7.5K, SV40, HSV, adenoviruses MLP, MMTV LTR and CMV promoters, may be used herewith, as well as promoters produced by recombinant DNA or synthetic techniques. Currently preferred promoters are those such as CMV, RSV LTR, the SV40 promoter alone, and the SV40 promoter in combination with the SV40 enhancer.

Exemplary tissue specific promoter/enhancer elements and transcriptional control regions that exhibit tissue specificity include, but are not limited to: the elastase I gene control region that is active in pancreatic acinar cells; the insulin gene control region that is active in pancreatic cells; the immunoglobulin gene control region that is active in lymphoid cells; the albumin, 1-antitrypsin and -fetoprotein gene control regions that are active in liver; the -globin gene control region that is active in myeloid cells; the myelin basic protein gene control region that is active in oligodendrocyte cells in the brain; the myosin light chain-2 gene control region that is active in skeletal muscle; and the gonadotropic releasing hormone gene control region that is active in the hypothalamus. U.S. application Ser. No. 08/631,334, filed Apr. 12, 1996 and PCT application Ser. No.

PCT/US97/07301, filed Apr. 11, 1997, are both incorporated herein by reference for the purposes of incorporating references even further describing the foregoing elements.

Specific initiation signals may also be required for sufficient translation of inserted protein coding sequences. These signals include the ATG initiation codon and adjacent sequences. In cases where the entire coding sequence, including the initiation codon and adjacent sequences are inserted into the appropriate expression vectors, no additional translational control signals may be needed. However, in cases where only a portion of the coding sequence is inserted, exogenous translational control signals, including the ATG initiation codon should be provided. The initiation codon must be in phase with the reading frame of the protein coding sequences to ensure translation of the entire insert. These exogenous translational control signals and initiation codons can be of a variety of origins, both natural and synthetic. The efficiency and control of expression may be enhanced by the inclusion of transcription attenuation sequences, enhancer elements, etc.

A variety of vectors may be used including, but not limited to, those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include gt10, gt11, gt18–23, ZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Vectors that allow for the in vitro transcription of RNA, such as SP6 vectors, may also be used to produce large quantities of RNA that may be incorporated into matrices.

The selected genes and DNA segments may also be in the form of a DNA insert located within the genome of a recombinant virus, such as, for example a recombinant herpes virus, retroviruses, vaccinia viruses, adenoviruses, adeno-associated viruses or bovine papilloma virus. While integrating vectors may be used, non-integrating systems, which do not transmit the gene product to daughter cells for many generations will often be preferred. In this way, the gene product is expressed during a defined biological process, e.g., a wound healing process, and as the gene is diluted out in progeny generations, the amount of expressed gene product is diminished.

In such embodiments, to place the gene in contact with a target cell, one would prepare the recombinant viral particles, the genome of which includes the gene insert, and contact the target cells or tissues via release from the polymer fiber of the present invention, whereby the virus infects the cells and transfers the genetic material. The following U.S. patents are each incorporated herein by reference for even further exemplification of viral gene therapy: U.S. Pat. No. 5,747,469, concerning adenovirus, retrovirus, adeno-associated virus, herpes virus and cytomegalovirus gene therapy; U.S. Pat. No. 5,631,236, concerning adenovirus gene therapy; and U.S. Pat. No. 5,672,344, concerning herpesvirus gene therapy.

Genes with sequences that vary from those described in the literature are also contemplated for use in the invention, so long as the altered or modified gene still encodes a protein that functions to effect the target cells in the desired (direct or indirect) manner. These sequences include those caused by point mutations, those due to the degeneracies of the genetic code or naturally occurring allelic variants, and further modifications that have been introduced by genetic engineering, i.e., by the hand of man.

Techniques for introducing changes in nucleotide sequences that are designed to alter the functional properties of the encoded proteins or polypeptides are well known in the art, e.g., U.S. Pat. No. 4,518,584, incorporated herein by reference, which techniques are also described in further detail herein. Such modifications include the deletion, insertion or substitution of bases, and thus, changes in the amino acid sequence. Changes may be made to increase the activity of a protein, to increase its biological stability or half-life, to change its glycosylation pattern, confer temperature sensitivity or to alter the expression pattern of the protein, and the like. All such modifications to the nucleotide sequences are encompassed by this invention.

It is an advantage of the present invention that one or more than one selected gene may be used in the gene transfer methods and compositions. The nucleic acid delivery methods may thus entail the administration of one, two, three, or more, selected genes. The maximum number of genes that may be applied is limited only by practical considerations, such as the effort involved in simultaneously preparing a large number of gene constructs or even the possibility of eliciting an adverse cytotoxic effect. The particular combination of genes may be chosen to alter the same, or different, biochemical pathways. For example, a growth factor gene may be combined with a hormone gene; or a first hormone and/or growth factor gene may be combined with a gene encoding a cell surface receptor capable of interacting with the polypeptide product of the first gene.

In using multiple genes, they may be combined on a single genetic construct under control of one or more promoters, or they may be prepared as separate constructs of the same of different types. Thus, an almost endless combination of different genes and genetic constructs may be employed. Certain gene combinations may be designed to, or their use may otherwise result in, achieving synergistic effects on cell stimulation and tissue growth, any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic segment or gene could be administered in combination with further agents, such as, e.g. proteins or polypeptides or various pharmaceutically active agents. So long as genetic material forms part of the composition, there is virtually no limit to other components which may also be included, given that the additional agents do not cause a significant adverse effect upon contact with the target cells or tissues. The nucleic acids may thus be delivered along with various other agents, for example, in certain embodiments one may wish to administer an angiogenic factor as disclosed in U.S. Pat. No. 5,270,300 and incorporated herein by reference.

As the chemical nature of genes, i.e., as a string of nucleotides, is essentially invariant, and as the process of gene transfer and expression are fundamentally the same, it will be understood that the type of genes transferred by the fiber matrices of the present invention is virtually limitless. This extends from the transfer of a mixture of genetic material expressing antigenic or immunogenic fragments for use in DNA vaccination; to the stimulation of cell function, as in wound-healing; to aspects of cell killing, such as in transferring tumor suppressor genes, antisense oncogenes or apoptosis-inducing genes to cancer cells.

By way of example only, genes to be supplied by the invention include, but are not limited to, those encoding and expressing: hormones, growth factors, growth factor receptors, interferons, interleukins, chemokines, cytokines, colony stimulating factors and chemotactic factors; transcription and elongation factors, cell cycle control proteins, including kinases and phosphatases, DNA repair proteins, apoptosis-inducing genes; apoptosis-inhibiting genes, oncogenes, antisense oncogenes, tumor suppressor genes; angiogenic and anti-angiogenic proteins; immune response stimulating and modulating proteins; cell surface receptors, accessory signaling molecules and transport proteins; enzymes; and anti-bacterial and anti-viral proteins.

F. Kits

All the essential materials and reagents required for the various aspects of the present invention may be assembled together in a kit. The kits of the present invention also will typically include a means for containing the vials comprising the desired components in close confinement for commercial sale such as, e.g., injection or blow-molded plastic containers into which the desired vials are retained. Irrespective of the number or type of containers, the kits of the invention are typically packaged with instructions for use of the kit components.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Fabrication of Polymer Fibers Containing Therapeutic Agents

Figure 8:
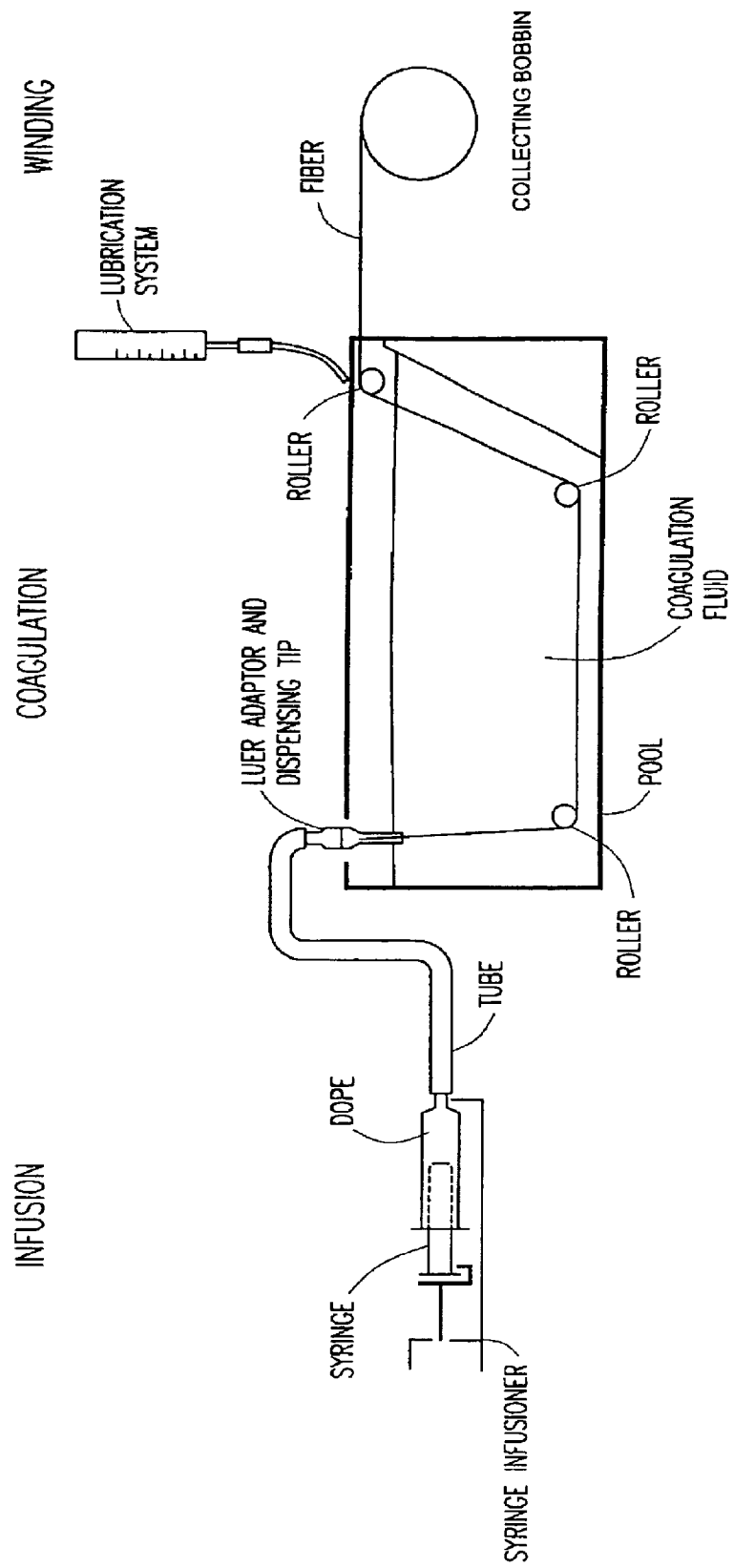
FIG. 8: Depicts an apparatus for fabrication of polymer fibers containing therapeutic agents.

In one embodiment of the present invention, the following procedure is used to create the drug-releasing fibers. The apparatus is depicted in FIG. 8. First, a biodegradable polymer such as poly(L-lactic acid) (PLLA), poly(DL-lactic acid), polycaprolactone, poly(glycolic acid), polyanhydride, or copolymers or blends of these or other biodegradable polymers are dissolved in some appropriate solvent (A) at concentrations ranging from 5 to 30 wt % depending on the type of polymer, 10 wt % being preferred for PLLA. In this embodiment, solvent (A) has low miscibility with water, and is very miscible with the coagulation bath solvent (B). Preferred choices of solvent (A) include chloroform and methylene chloride. Once the polymer is dissolved, an aqueous solution containing both the biomolecules(s) of interest and a surfactant, is added to the polymer solution. The concentration of the aqueous emulsion is typically in the range of 1 to 50% v/v of the polymer solution, 4–10% being most typical for monofilament PLLA fibers. The surfactant can be one or a combination of substances familiar to those skilled in the art, such as bovine serum albumin (BSA), poly(vinyl alcohol), pluronics, or biological surfactants such as the family of phospholipids. Other surfactants not specifically mentioned here, but known to those skilled in the art are included by extension. In a typical use, BSA is used as the surfactant at concentrations ranging from about 10 fold to 100 fold higher than the biological molecule of interest, with typical concentrations ranging from 10 wt % to 50 wt % of the aqueous phase.

Using some form of mechanical energy such as sonication, vortexing, or shear forces generated by forcing the liquid through a small orifice, a water-in-oil type emulsion is formed between the aqueous and organic phases. This emulsion must be stable for periods far in excess of time required for extrusion. The size of the dispersed aqueous phase droplets is primarily dependent on the quality of the surfactant, and the amount of mechanical energy imparted to the system in forming the emulsion. The aqueous phase size is an important variable in both release kinetics and mechanical properties of the fiber.

The emulsion is then extruded into a coagulating bath containing solvent (B). The polymer emulsion is extruded into the coagulation bath through a dispensing tip ranging in size from 16 gage down to 30 gage. Solvent (B) must be highly miscible with solvent (A), and must be a non-solvent for the polymer; isopropyl alcohol is the most typical choice but any solvent that is a non-solvent for the polymer and highly miscible with solvent (A) will work. For example hexane is very miscible with methylene chloride yet is a non-solvent for the polymer, therefore, methylene chloride and hexane make a good solvent and coagulating bath combination. Because solvent (A) is highly miscible with coagulating bath solvent (B), it freely diffuses from the polymer solution stream, into the coagulating bath. The polymer, however, is not soluble in solvent (B), and therefore begins to precipitate upon itself, forming the outer sheath of a fiber and trapping virtually all of the dispersed aqueous phase of the emulsion within the forming fiber. In this way, the fiber is loaded with the drug or protein of interest. The forming fiber may be passed over a series of rollers within the coagulation bath to provide a fixed path length through the coagulation bath should a fixed path length be desired. The fiber is drawn from the coagulation bath at a determined rate. In the laboratory, the inventors have used a cylinder attached to a modified variable-speed lathe that can accurately maintain its angular velocity. The drawn and extruded fiber is then removed from the cylinder and either freeze-dried, frozen, or oven dried and placed in a desecrator or freezer, depending upon recommended storage conditions of the loaded biomolecules.

Figure 9A:
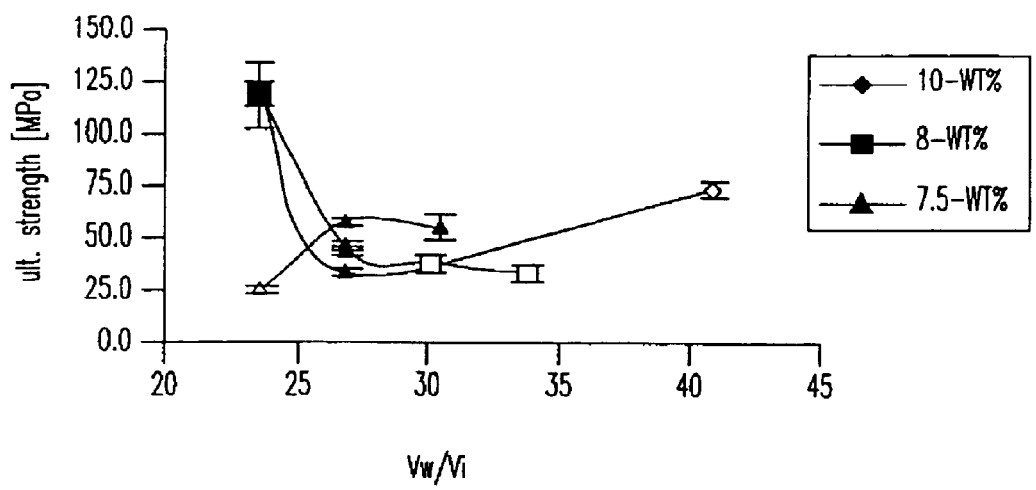
FIG. 9A and FIG. 9B: By varying the ratio of the infusion speed of the polymer emulsion into the coagulating bath to the linear winding speed of the lathe, very surprising changes in the mechanical properties was observed.
Figure 9B:
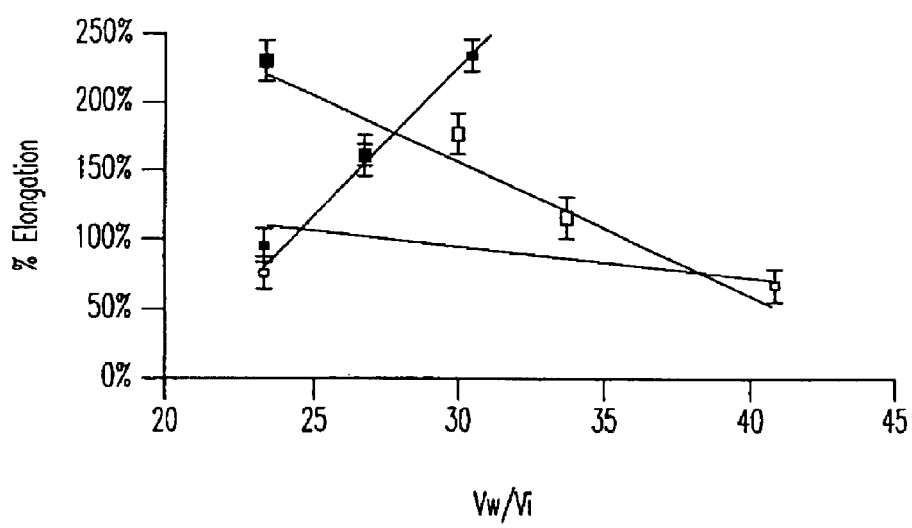
Figure 10A:
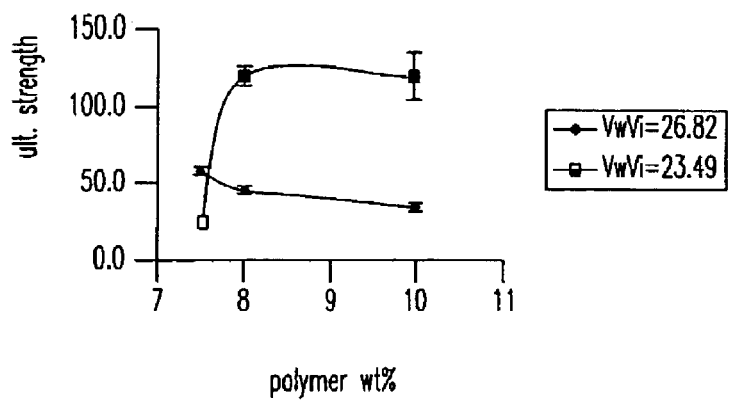
FIG. 10A and FIG. 10B: The mechanical properties of fibers change as a function of polymer solvent(s), coagulating bath solvent(s), interaction of the solvent system, winding speed to infusion speed ratio, total time in the coagulating bath, ratio of aqueous phase to polymer solution phase in emulsion, and the quality of the surfactant.
Figure 10B:
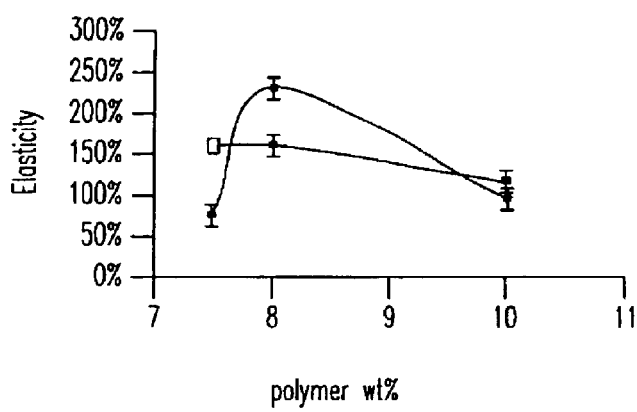

By varying the ratio of the infusion speed of the polymer emulsion into the coagulating bath to the linear winding speed of the of the lathe, very surprising changes in the mechanical properties of the fibers have been found, as shown in FIGS. 9A and 9B. The mechanical properties of the fibers change as a function of the following variables: polymer solvent(s), coagulating bath solvent(s), intermiscibility of the solvent system, winding speed to infusion speed ratio, total time in the coagulating bath, ratio of aqueous phase to polymer solution phase in the emulsion, and the quality of the surfactant. Changes in mechanical properties as a function of several of these variables are shown in FIGS. 10A and 10B.

Figure 11A:
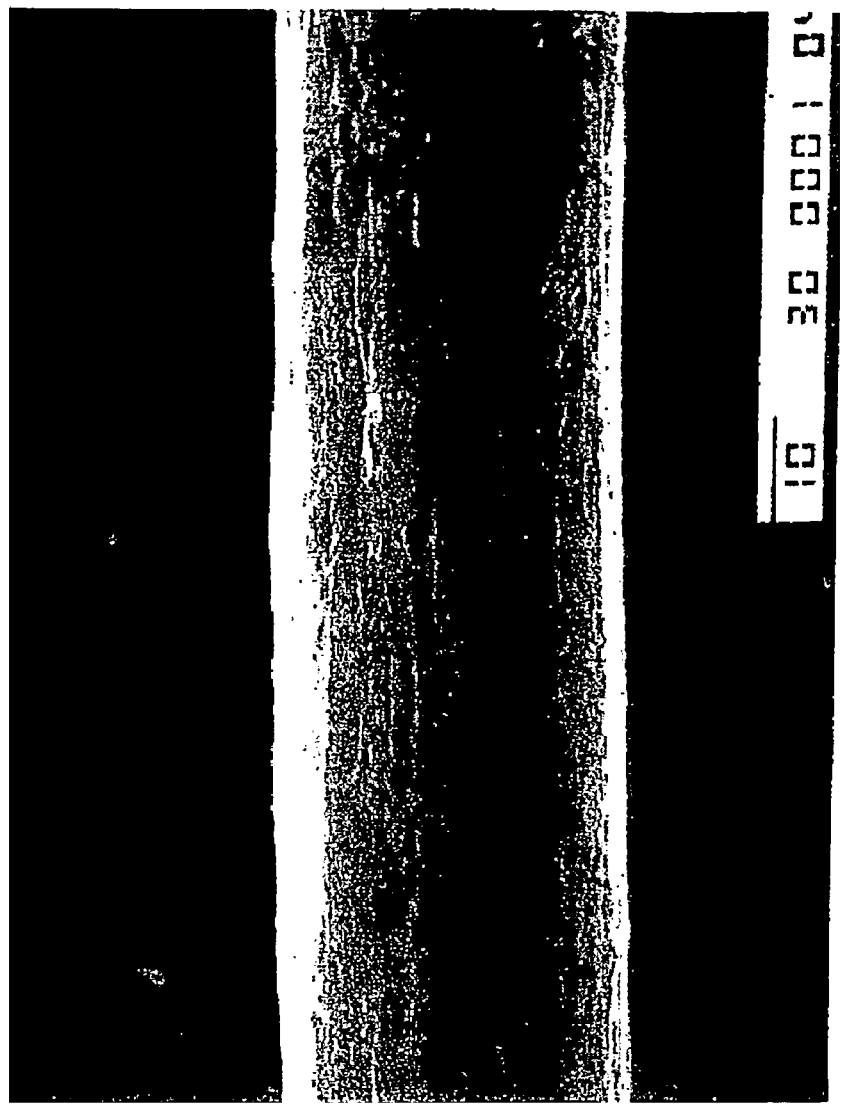
FIG. 11A, FIG. 11B and FIG. 11C: Fibers have been produced with varying surface textures.
Figure 11B:
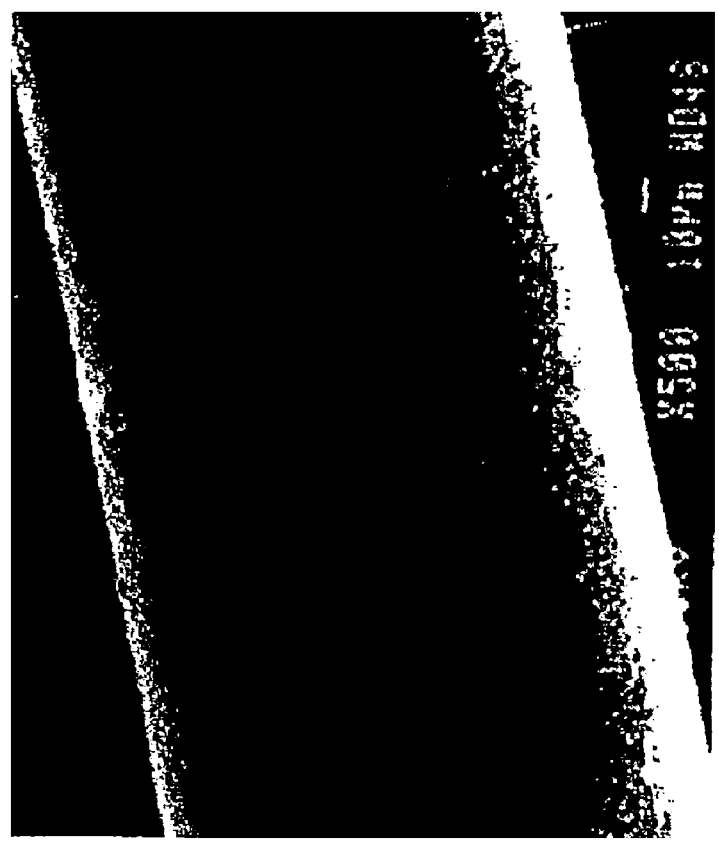
Figure 11C:

Another surprising discovery was that the surface texture of the finished fiber could also be controlled by appropriate choices of solvent and polymer systems. The inventors have produced fibers with surface textures that vary from smooth, to veloured, to longitudinally grooved as shown in FIGS. 11A–11C. These changes in surface texture have practical applications to cell growth in providing surfaces with greater adhesive properties in the case of the veloured texture, and better contact guidance in the case of the longitudinally grooved fibers. All of the changes in mechanical properties and surface texture significantly affect the release kinetics of therapeutic agents.

Figure 12:
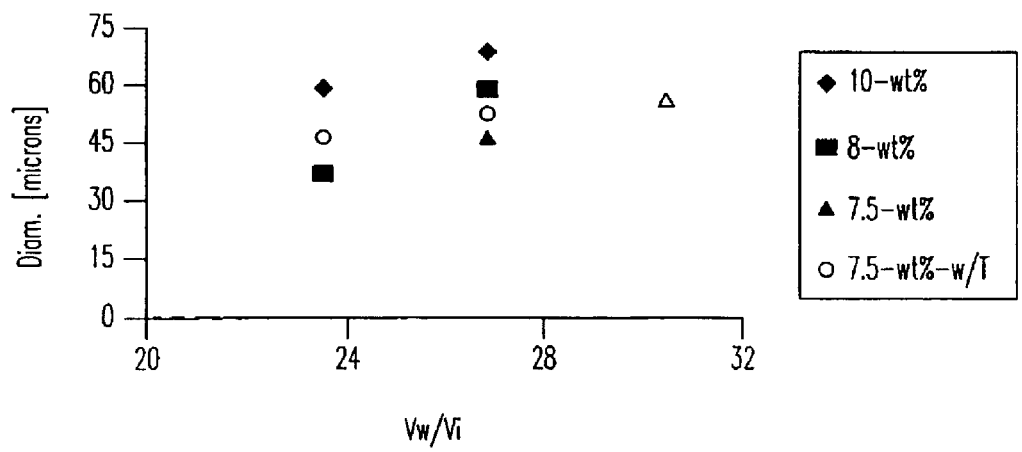
FIG. 12: Illustrates variations in the diameter of fibers as a function of the winding speed to infusion speed ratio (Vw/Vi) and of weight percent.

The diameter of the fibers has been controlled by processing conditions as shown in FIG. 12. Because the processing parameters that control the mechanical properties, surface texture, diameter, and release kinetics are known fibers with specific properties for specific uses can be tailor made.

That biological therapeutic agents retain biological activity throughout this fabrication process can be shown with a sandwich ELISA where the agent loaded into the fiber was the Fab fragment of mouse IgG. For the ELISA to detect the presence of the Fab fragment, the biological activity of both binding epitopes must be maintained.

In another embodiment of the fabrication process, a poor solvent for the polymer is added to the polymer solution such as toluene. The addition of the poor solvent changes the mechanical properties of the fiber.

In another fabrication embodiment, up to 20% v/v of the polymer solvent is added to the coagulation bath solvent. The addition of the polymer solvent decreases the concentration gradient from inside the fiber to outside the fiber. This changes the diffusion rate and hence the rate at which the outer sheath of the fiber forms. The rate of this outer sheath formation is critical to the surface texture of the fibers and the mechanical properties of the fiber, and to the release kinetics of the biomolecule.

In another fabrication embodiment, a thickening solution, such as glycerol, is added to the coagulation bath. This increases the viscosity of the coagulation bath, and changes the specific gravity of the coagulation bath. Both of these variables have resulted in substantially increased ability to form loaded fibers. The concentration of glycerol varies from 8 to 20% v/v.

Alternatively, coaxial fibers can be fabricated in a single process by methods familiar to those skilled in the art of extrusion. Using these techniques, various polymer(s) and biomolecule(s) can be added in each layer of the coaxial fiber.

Example 2

Figure 13:
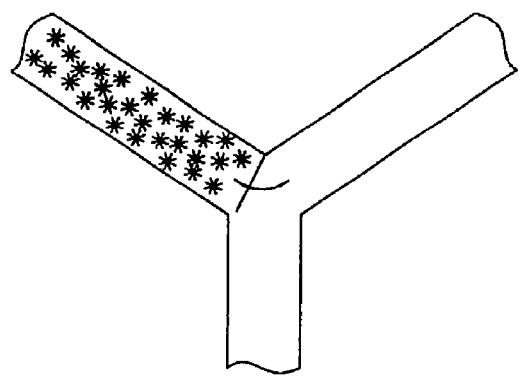
FIG. 13: Illustrates the use of a butterfly valve at a "Y" junction to gradually change the ratio of two solutions to achieve a concentration gradient down the length of a fiber.
Figure 14:
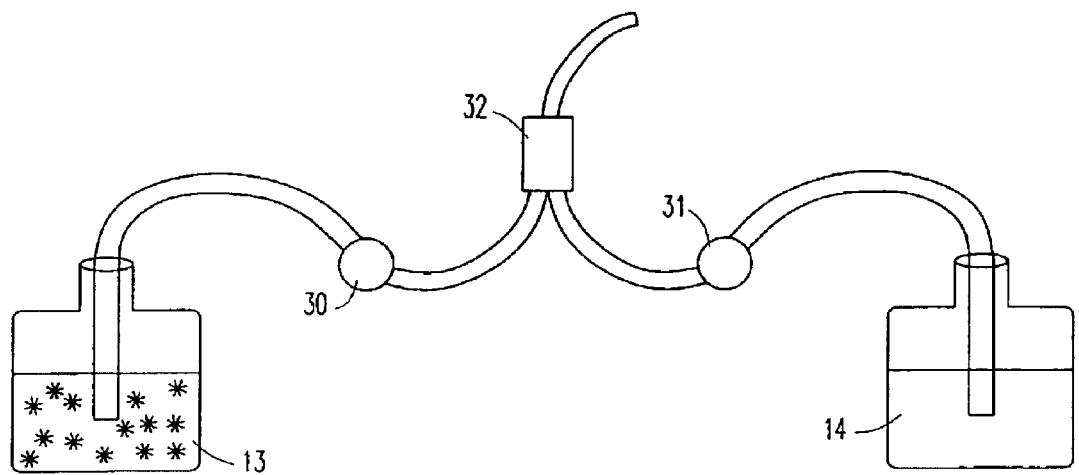
FIG. 14: Illustrates the use of independent pumps and a mixing chamber to establish a well-controlled gradient with known change in concentration per centimeter length. The numerals 13 and 14 denote polymer solutions, with and without therapeutic agents respectively, 30 denotes pump 1, 31 denotes pump 2 and 32 denotes the mixing chamber.

Fabrication of Polymer Fibers Containing Variable Concentrations of Therapeutic Agents In another fabrication embodiment, the process is similar to that described in Example 1, with the exception that a concentration gradient is applied down the length of the fiber. This is accomplished by having two solutions. One is a polymer emulsion containing the therapeutic agent(s) of interest, and the other does not contain therapeutic agents, or contains different biomolecules. The gradient is accomplished by continuously changing the ratio of the two solutions during the extrusion process. This can be accomplished in a number of ways including a butterfly valve at a "Y" junction as shown in FIG. 13, or using independent pumps with or without a mixing chamber as shown in FIG. 14. In this way, a well-controlled gradient is established with known change in concentration per centimeter length. Another embodiment of the present invention is the creation of "banded" fibers. In banded fibers, there are several possible configurations; in one embodiment, both polymer solutions are emulsions containing different biomolecules. This is accomplished in the same way as the gradient, where the gradient is a series of step-functions, switching alternately from emulsion A to emulsion B.

In a second embodiment, one of the bands if from a polymer emulsion containing one or more biomolecules as in other embodiments described herein. The other band is a polymer segment that acts as a sealant so that the finished fibers can be cut to pre-specified lengths so that each end of the finished fibers will be sealed at both ends. In each of these embodiments, the band lengths are independently adjustable. These gradient and banded fibers may be used with or without a concentric coating as described in the next example.

Example 3

Fabrication of Polymer Fibers with Concentric Coatings

In yet another fabrication embodiment, a pre-existing fiber is loaded through a spinneret and through the coagulation bath. The liquid polymer emulsion is added in a "T" or "Y" junction and coats the fiber before entering a coagulation bath. Thus concentric coatings are applied to the fiber, with each coating having the ability to contain a different therapeutic agent(s) as shown in FIG. 4. The coating polymer may be the same or different from the core polymer. There may be molecules attached to the core fiber to increase the adhesion of the coating polymer. For example, a thin layer of BSA, may improve the adhesion of chitosan to poly(L-lactic acid). By an intricate spinneret, two or more polymer emulsions each containing a different biomolecule can be put in the coating. This is accomplished by bringing all coating materials into the spinneret, with baffles separating each coating polymer stream. This allows fibers to release different molecules as a function of angular position around the fiber. In certain embodiments, the spinneret may have a non-circular shape, thereby forming fibers with any desired cross-sectional shape. This is true of the core fiber as well as the coating polymers.

An alternative fabrication technique is to use specially designed multilumen spinnerets to create standard fiber structures well known to those familiar in the art, such as core and sheath, islands in the sea, etc.

Example 4

Fabrication of Environmentally Responsive Polymer Gel Fibers

In a different fabrication embodiment, environmentally responsive polymer hydrogels are formed in nanosphere size by emulsion polymerization or other methods. Such nanospheres are then incorporated into fibers. "Environmentally responsive gels" are intended to represent polymer gels that exhibit a substantial change in their physical characteristics as the environment surrounding the gels undergoes relatively small changes. Polymer hydrogels that have been found to be useful in the present invention include poly(N-isopropylacrylamide) (NIPA) and poly(acrylic acid) (PAA) gels. For example, NIPA gels have the ability to undergo dramatic volume changes of 100 fold in response to a small (2–3C.) temperature change. These nanospheres may be loaded with biological molecules by soaking them in an aqueous solution of the biomolecules. These loaded nanospheres are then dried and added to the polymer solution with or without forming an emulsion. All other fabrication processes are the same. This process then creates a fiber that is temperature sensitive. The NIPA phase transition can be adjusted by those skilled in the art to occur at 38–39C. This now provides a fiber that is responsive to the physiological state of the patient. It has a dramatic increase in release kinetics if the patient begins to run a fever, and because this is a reversible phenomenon, the release kinetics slow down again once body temperature returns to normal.

Example 5

Chitosan Based Fibers

Figure 1:
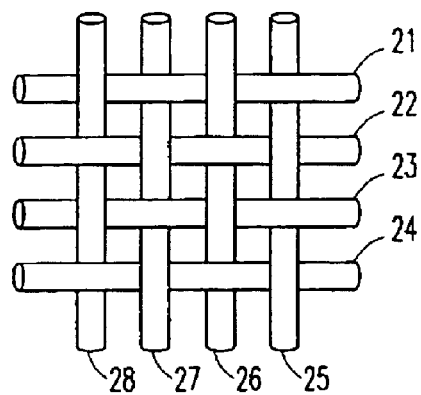
FIG. 1: Shows fibers configured in a complex three-dimensional woven scaffolding with patterning. Each of the individual fibers may be loaded with one or more therapeutic agents.
Figure 2:
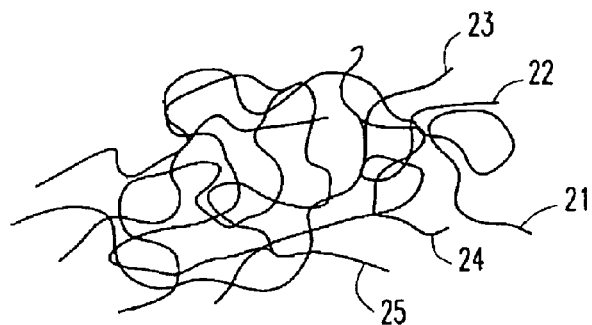
FIG. 2: Shows fibers configured in a three-dimensional non-woven scaffolding without patterning. Each of the individual fibers may be loaded with one or more therapeutic agents. All fibers may contain the same therapeutic agent(s) or, a variety of different agents may be used in other fibers in the same scaffolding. The numerals 21–25 denote fibers loaded with therapeutic agents.

In another fabrication embodiment, rather than ester based synthetic polymers described above, naturally occurring polysaccharides such as chitosan may be used as the polymer system. It is well known in the art that chitosan fibers can be made by dissolving the chitosan in 3% acetic acid, and using 5% sodium hydroxide as the coagulation bath. The inventors have found that one can use 1% hydrochloric acid to dissolve the chitosan, that the chitosan concentrations can go as low as 2.5 wt %, and good quality fibers are obtained if the coagulation bath consists of Tris base in concentrations ranging from 5 to 15% (FIG. 1). This is the first reporting of chitosan fibers extruded under these conditions.

Chitosan is a biodegradable polymer. Chitosan is enzymatically degraded by lysozyme, which is present in plasma, in the interstitial fluid, as well as intracellularly. Since the action of lysozyme on chitosan is dependent on the presence of acetyl groups on the polymer backbone, one can modulate, under specific circumstances, the release rate of the fibers described above by two alternative ways: a) one is to extrude fibers as described above from a heterogeneous mixture consisting of chitosan polymers each with a different degree of deacetylation. In this way, one can maintain the level of released drug in the optimal range for the necessary period of time; b) another possibility is to extrude segmented fibers of chitosan, wherein each segment is made from chitosan having a different degree of deacetylation as described in FIG. 2. This latter approach can have applications for migratory cells by creating a temporal gradient along the fiber.

The inventors have also mixed reconstituted basement membrane extract (matrigel, Becton Dickinson, Bedford, Mass.) with chitosan dissolved in hydrochloric acid, and have demonstrated the ability to extrude good quality fibers using a coagulation bath consisting of Tris base in concentrations ranging from 10 to 15%. In this case, it was found that axonal extension was improved over chitosan alone. ELISA confirmed the presence of the two major proteins of matrigel (laminin and collagen type IV) in the fibers. These proteins also retained biological activity as demonstrated by in vitro neuron attachment and axonal extension. Another possibility is to coat the same Tris base extruded chitosan fibers with matrigel.

In a surprising finding, if the inventors sulfate the chitosan prior to adding the matrigel, neuron attachment and axon extension are improved dramatically compared to the case of matrigel and untreated chitosan (FIG. 3, FIG. 4). Using the same chemical extrusion conditions, the inventors could extrude polymer fibers made of 0.2% sulfated chitosan with 3.2% unmodified chitosan with or without matrigel as a co-extruded substance.

It is well known in the art that sulfated chitosan has heparin-like, anticoagulant properties due to their similar chemical structure. The fibers made of unmodified chitosan dissolved in hydrochloric acid and extruded in Tris base can be coated with sulfated chitosan or with matrigel and sulfated chitosan. This may yield fibers with inherent anticoagulant properties that can also be loaded with active drugs. This may have substantial clinical application in fabricating vascular stents and other medical devices that come in direct contact with blood, and require mechanical strength, and/or the ability to deliver drugs.

The relatively harsh acidic and basic environment in which chitosan fibers are extruded as described above substantially limits the range of biomolecules that can be incorporated into the fiber to only those biomolecules that can withstand very large pH transitions. Therefore, to overcome this inherent limitation, the inventors have developed a new approach to retain the bioactivity of even the most sensitive biomolecules loaded into chitosan fibers. In this embodiment, sensitive biomolecules of interest are loaded into PLLA microspheres using solvent evaporation or other techniques well known in the drug delivery literature. These PLLA microspheres are then mixed with 3.5 wt % chitosan solution and extruded as described above. A chitosan fiber loaded with PLLA microspheres will form when this mixture is extruded using either acetic acid and sodium hydroxide or 1.2% hydrochloric acid and 10 to 15% Tris base. The PLLA microspheres can protect the sensitive biomolecules from the harsh processing conditions of the chitosan fibers.

Example 6

Neural Tissue Engineering

Figure 15:
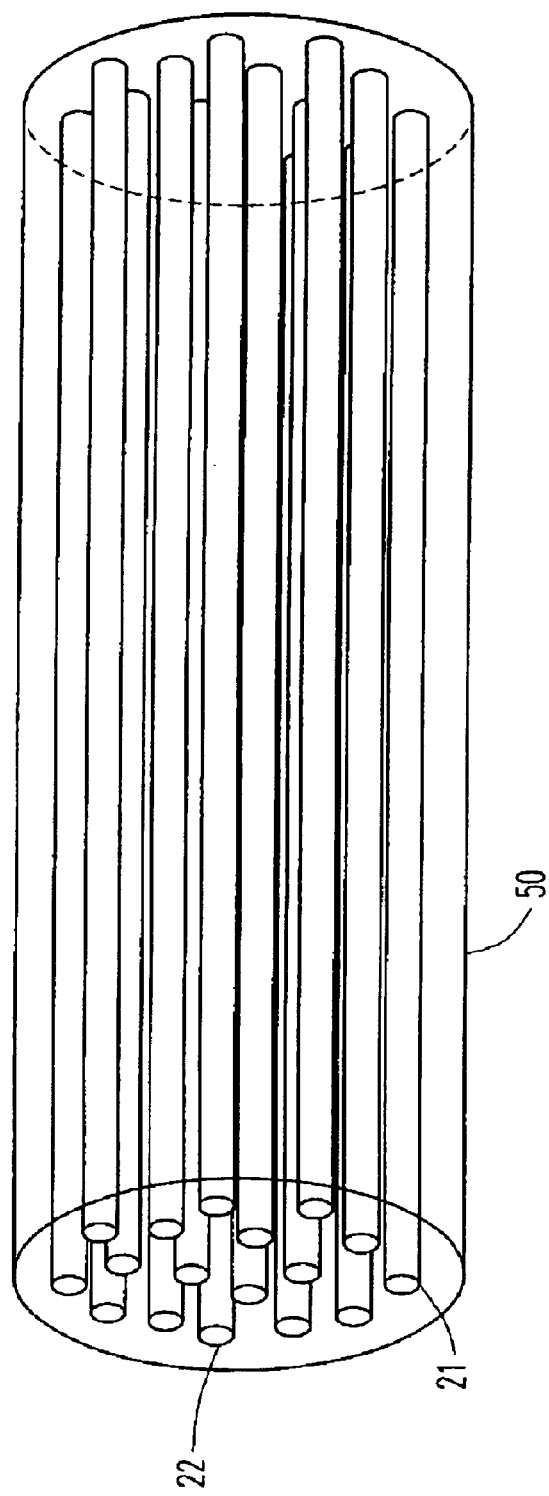
FIG. 15: Illustrates parallel arrays of fibers packed into silicon rubber of other suitable material tubes and loaded with neutrophins for axonal growth. The numeral 21 denotes fibers loaded with neutrophins, 22 denotes fibers loaded with other cytokines or growth factors, and 50 denotes a tube (made from silicone rubber or other material) to hold the fiber bundle in place.

In this aspect of the present invention, parallel arrays of fibers are packed into silicon rubber or other suitable material tubes and loaded with neurotrophins for axonal growth as shown in FIG. 15. These bundles of fibers are placed in severed peripheral or central nerves. The neurotrophins may be loaded in a linear or some other appropriate gradient. This device is implanted bridging the gap between the ends of the nerve stumps. As the fibers release neurotrophins, axons begin to migrate out of the proximal end, across the fiber bundle and into the distal nerve end. Once in the distal end, guidance cues are provided by existing Schwann or glial cells and reconnections can then be made. It has been previously found that axons receive contact guidance by these fiber bundles and are able to traverse at least 1.8 cm in a rat sciatic nerve resection using non-loaded fibers. The optimal density of unloaded fibers in the tube is approximately 32 fibers in a 1.5 mm diameter tube for rat sciatic nerve growth.

Example 7

Preparation and use of Polymer Fiber Stents

In another embodiment, fibers can be loaded with a drug of interest and used in stents or other medical devices where mechanical strength is required. The stents can be woven in such a manner as to have loaded fibers intermingled with unloaded fibers if needed for mechanical properties.

Fibers can also be used in conjunction with commercially available stents to deliver drugs at the placement site. In this case, the fibers would not provide any mechanical support, but would only serve as a drug delivery reservoir.

Example 8

Preparation and use of Wound Dressings

In another embodiment, a gauze or dressing can be made from these fibers. This dressing can have two sides, an upper surface that will release molecules for re-epithelialization and provide a substrate for these cells. The bottom surface will promote regeneration of dermal tissue. This dressing is designed for dermal wound healing, including burns, full thickness dermal wounds and chronic or non-healing wounds and sores. Each fiber can be coated to provide temporal release of drugs or factors to correspond to the three phases of dermal wound healing.

For example, in the case of a dressing designed for trauma patients, the first chemical to be released could be a pro-coagulant to help stop the bleeding. The next layer could then release cytokines to help recruit neutrophils and macrophages for the next phase of wound healing. Finally, a release of factors to help with reducing excessive scar tissue and to inhibit contractions, which are particularly disabling to burn patients.

Example 9

Fabrication of Artificial Arteries

It may be possible to construct an artificial artery using techniques described herein. A series of hollow, cylindrical sections can be knitted, woven, braided or fabricated using non-woven technology with fibers loaded with various biological agents. The innermost cylinder is preferably tightly woven and contains drugs or agents to promote migrating, spreading and functioning of an intact endothelial cell layer. The next cylinder is composed of a woven or knitted architecture with fibers predominately circumferentially wound around the inner cylinder. This layer will induce the migration and proliferation of smooth muscle fibers, and promote the expression of elastin to create the internal elastic media. The next cylinder is composed of knitted or non-woven fibers and will contain drugs to promote the ingrowth of fibroblasts, macrophages and the creation of extracellular matrix. The last layer will compose longitudinal fibers that will promote the vascularization of the arterial cells via an artificial vasa vasorum, created by VEGF releasing fibers, or other promoters of angiogenesis.

Example 10

Drug Delivery Scaffold

In another application embodiment, these fibers can be used for drug delivery scaffolds in places where a fiber format is preferred to that of a microsphere. For example, for drug delivery directly to the blood stream, a fiber can be attached to a vessel wall, and be contained entirely within the blood vessel. Microspheres cannot flow through the circulatory system, as they will become trapped at some level, potentially compromising the downstream tissue. The fibers, however, can release drugs and not cause any problems with occluding downstream branches so long as the fiber remains intact. Other locations where a fiber may make more sense than microspheres may include the eye, where the spheres may be more likely to interfere with the subject's vision. A fiber could be tacked down and not float into the field of view. Fibers may be able to stay in place better than microspheres, particularly within a space where the fiber can be coiled. In this way, the mechanical tension within the fiber will cause it to push against the sides of the tissue space and thus remain in position.

Example 11

In Situ Arteriogenesis

Similar in scope to example 9, is in situ arteriogenesis. In this embodiment, a fiber bundle containing VEGF or a similar substitute is placed into the body with both ends of the fiber bundle near or touching an existing blood vessel. As the fiber begins to release VEGF or its substitute, endothelial cells from the existing blood vessel will be induced to migrate out from the existing vessel following a process similar to normal angiogenesis. The leading endothelial cells will traverse the path of the fiber bundle, thus creating a new blood vessel along the path of the fiber bundle. This fiber bundle may have several forms, it may exist of single or a few fibers that only release VEGF or its substitute, or it may be a tube with VEGF or similar growth factor that is chemotactic for endothelial cells on the inside, and a different factor for smooth muscles on the outside. In this way, the size of the created vessel may be determined. In this application, cells are guided into initially cell-free scaffoldings by cell-specific growth factors.

Example 12

Bone Fracture Healing

In another wound healing embodiment, proteins known to enhance bone fracture healing are loaded into a fiber. This fiber can then be wrapped around the bone at the site of the fracture, releasing the growth factors and enhancing the rate of fracture repair.

These fibers can either be in a helical structure (single or multiple helix), or they may be woven into a loose, open weave. Either in the helical or in the woven format, the fibers are placed around the bone fragments, holding them in place while releasing their growth factors.

In the case of a non-healing fracture that is due to lost or poor blood supply to the fracture site, a fiber or set of fibers containing VEGF or its equivalent may be used to enhance blood supply to the fractured area.

In this embodiment, bone fractures may be healed at accelerated rates compared to non-treated fractures, and non-unions may be healed in certain cases.

Example 13

Skin Ulcer Healing

Similar to example 8 which described one form of dermal wound healing, another important example of this technology is the potential of healing chronic skin ulcers of various origins, such as diabetic foot ulcers, venous ulcers and general pressure sores. These conditions, and potentially other similar conditions may be healed based on creating a non-woven mesh of fibers that release factors known to accelerate dermal wound healing, for example, platelet derived growth factor (PDGF), transforming growth factor-beta (TGF-beta), and VEGF or similar protein. This non-woven mesh can be inserted or packed directly into the ulcer or wound, where these growth factors can help accelerate the wound-healing process. These dressings can be designed for healing dermal sores and ulcers. In this case, there is little need to reduce bleeding; rather one of the biggest needs of these patients, particularly those with diabetic ulcers is lack of blood supply to the wound site. Therefore, factors that induce angiogenesis may be able to increase circulation and help to rejuvenate the tissue at the site of the sore or ulcer.

Each dressing can be designed for the particular needs of the various types of wounds or sores by altering the biomolecules that are released, and the kinetics at which they are released.

Example 14

Muscle Grafts

In another embodiment, parallel arrays of fibers may be loaded with muscle stem cells. These stem cells can be of cardiac, smooth or skeletal muscle origin. Once these muscle stem cells are seeded onto the fiber array, the fibers can be mechanically stretched in vitro to help these cells align and differentiate properly. Alignment may also be achieved by using fibers of very small diameter. Our experience with axons indicates that with fibers on the order of 50 µm diameter tend to help cells align parallel to the axis of the fibers. Other fibers in this bundle can release angiogenic factors to create a vascular supply for the muscle cells. In the case of skeletal or smooth muscle tissue, fibers for nerve growth can also be included to induce the formation of neuromuscular junctions. Various experimental conditions used to harvest, isolate, reproduce and differentiate these stem cells are known to those skilled in the art, and is not a part of this patent.

Example 15

Alternative Fiber Fabrication Procedure 1

To fabricate small volumes of polymer on the order of 100 µl of polymer solution, the following method has been developed. Create the emulsion as described in example 1. Add this emulsion to a small container, such as a 1 ml FALCON® tube that has been modified by inserting a 20 to 30 gauge needle through the bottom of the tube, 23 gauge being most typical. Place this tube into a modified 50 ml tube that is full of the coagulating bath solvent. Place the tubes in a centrifuge and spin between 500 to 1200 rpm, 700 being most typical. The centrifugal force will push the small volume of polymer emulsion through the needle and into the coagulating fluid. By similar solvent exchanges as described in example 1, a fiber is formed. This method uses substantially less polymer emulsion with very little wasted emulsion.

Example 16

Alternative Fiber Fabrication Procedure 2

As an alternative fabrication procedure, the coagulation solvent(s) are flowed through long vertical tubes at a prescribed rate and the polymer solution is extruded into the flowing stream of coagulation solvent(s). The flow from the tube exits into a bath. The fiber passes over one or more bobbins and is taken from the bath and wound onto a spool. The solvent flow rate, the rate of polymer extrusion, the composition of the polymer solution/emulsion, the composition of the coagulating bath solvent(s), the rate at which the fiber is wound, any drawing that may take place between successive bobbins, and any additional baths or treatments will affect the fiber mechanical and chemical properties as well as the release kinetics of the loaded biological materials.

Example 17

Treatment of Glaucoma

Similar to drug delivery in the eye, described in example 10, and the neural stent described briefly in example 6, glaucoma may be treated by combining an intraocular drug delivery with a neural treatment applied to the optic nerve. Retinal ganglion cells undergo apoptosis leading to death of the axons of the optic nerve. It is hypothesized that if the cells could be supported both within the eye as well as along the path of the optic nerve, the cells may be able to survive. A fiber bundle that releases growth factors such as NT-4, BDNF, CNTF, may be applied topically to the exterior of the optic nerve. Simultaneously, fibers that release apoptosis inhibitors, or factors to support the retinal ganglion cells are implanted within the eye. This combined effort may prolong or save the sight of those suffering from glaucoma.

As is seen from the preceding examples, other tissues, organs, or structures are possible to weave once the basic physiologic structure is understood. This can be extended to organs of the digestive system, musculoskeletal system, urological system, circulatory system, nervous system.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Aigner, Tegeler, Hutzler, Campoccia, Pavesio, Hammer, Kastenbauer, Naumann, "Cartilage tissue engineering with novel nonwoven structured biomaterial based on hyaluronic acid benzyl ester," *J. of Biomed. Materials Res.*, 42(2):172–81, 1998.

Auerbach and Auerbach, "Angiogenesis inhibition: a review," *Pharmac. Ther.*, 63:265, 1994.

Breitbart, Grande, Kessler, Ryaby, Fitzsimmons, Grant, "Tissue engineered bone repair of calvarial defects using cultured periosteal cells," *Plastic & Reconstructive Surgery*, 101(3):567–74, 1998.

Cao, Rodriguez, Vacanti, Ibarra, Arevalo, Vacanti, "Comparative study of the use of poly(glycolic acid), calcium alginate and pluronics in the engineering of autologous porcine cartilage," *J. of Biomaterials Sci., Polymer Edition*, 9(5):475–87, 1998.

Dillon, Yu, Sridharan, Ranieri, Bellamkonda, "The influence of physical structure and charge on neurite extension in a 3D hydrogel scaffold," *J. of Biomaterials Sci., Polymer Ed.*, 9(10):1049–69, 1998.

Elcin, Dixit, Lewin, Gitnick, "Xenotransplantation of fetal porcine hepatocytes in rats using a tissue engineering approach," *Artificial Organs*, 23(2):146–52, 1999.

Fauza, Fishman, Mehegan, Atala, "Videofetoscopically assisted fetal tissue engineering: skin replacement," *J. of Pediatric Surgery*, 33(2):357–61, 1998.

Fidler and Ellis, "The implications of angiogenesis for the biology and therapy of cancer metastasis," *Cell*, 79:185, 1994.

Folkman and Klagsbrun, "Angiogenic factors," *Science*, 235:442–447, 1987.

Folkman, "How is blood vessel growth regulated in normal and neoplastic tissue," *Cancer Res.*, 46:467, 1986.

Folkman, J., "Angiogenesis in cancer, vascular, rheumatoid and other disease," *Nature Med.*, 1:27, 1995.

Grande, Halberstadt, Naughton, Schwartz, Manji, "Evaluation of matrix scaffolds for tissue engineering of articular cartilage grafts," *J. of Biomed. Mat. Res.*, 34(2):211–20, 1997.

Gutsche, Lo, Zurlo, Yager, Leong, "Engineering of a sugar-derivatized porous network for hepatocyte culture," *Biomaterials*, 17(3):387–93, 1996.

Hoerstrup, Zund, Lachat, Schoeberlein, Uhlschmid, Vogt, Turina, "Tissue engineering: a new approach in cardiovascular surgery-seeding of human fibroblasts on resorbable mesh," *Swiss Surgery,* (Suppl.), 2:23–5, 1998.

Hoerstrup, Zund, Schoeberlein, Ye, Vogt, Turina, "Fluorescence activated cell sorting: a reliable method in tissue engineering of a bioprosthetic heart valve," *Annals of Thoracic Surgery,* 665(5):1653–7, 1998.

Isogai, Landis, Kim, Gerstenfeld, Upton, Vacanti, "Formation of phalanges and small joints by tissue-engineering," *J. of Bone & Joint Surgery, American Vol.,* 81(3):306–16, 1999.

Martin, Padera, Vunjak-Novakovic, Freed, "In vitro differentiation of chick embryo bone marrow stromal cells into cartilaginous and bone-like tissues," *J. of Orthopaedic Res.,* 16(2):181–9, 1998.

Nagy et al., "Pathogenesis of ascites tumor growth: vascular permeability factor, vascular hyperpermeability, and ascites fluid accumulation," *Cancer Res.,* 55:360, 1995.

Peppas and Langer, "New challenges in biomaterials," *Science,* 263:1715–1720, 1994.

Peter, Miller, Yasko, Yaszemski, Mikos, "Polymer concepts in tissue engineering," *J. of Biomed. Materials Res.,* 43(4):422–7, 1998.

Sacks, Chuong, Petroll, Kwan, Halberstadt, "Collagen fiber architecture of a cultured dermal tissue," *J. of Biomed. Engineering,* 119(1):124–7, 1997.

Sambrook et al., *Molecular Cloning: A Laboratory Manual*, Cold Spring Harbor Laboratory Press, Cold Spring Harbor, N.Y., 1989.

Shinoka, Shum-Tim, Ma, Tanel, Isogai, Langer, Vacanti, Mayer, "Creation of viable pulmonary artery autografts through tissue engineering," *J. of Thoracic & Cardiovascular Surgery,* 115(3):536–45, 1998.

Sims, Butler, Cao, Casanova, Randolph, Black, Vacanti, Yaremchuk, "Tissue engineered neocartilage using plasma derived polymer substrates and chondrocytes," *Plastic & Reconstructive Surgery,* 101(6):1580–5, 1998.

Vunjak-Novakovic, Obradovic, Martin, Bursac, Langer, Freed, "Dynamic cell seeding of polymer scaffolds for cartilage tissue engineering," *Biotechnology Progress,* 14(2):193–202, 1998.

Whang, Tsai, Nam, Aitken, Sprague, Patel, Healy, "Ectopic bone formation via rhBMP-2 delivery from porous bioabsorbably polymer scaffolds," *J. of Biomed. Materials Res.,* 42(4):491–9, 1998.

Wong and Mooney, "Synthesis and properties of biodegradable polymers used in tissue engineering," *In: Synthetic Biodegradable Polymer Scaffolds*, (Atala and Mooney, eds.), Birkhauser Press, Boston, Mass, pp. 51–82, 1997.

Yoo and Atala, "A novel gene delivery system using urothelial tissue engineered neoorgans," *J. of Urology,* 158(3 Pt 2):1066–70, 1997.

What is claimed is:

1. A method of extruding a drug releasing fiber from chitosan comprising use of hydrochloric acid as a solvent and Tris base as coagulating bath.

2. The method of claim 1, wherein the hydrochloric acid concentration is from about 0.25% to about 5%.

3. The method of claim 1, wherein the tris base concentration is from about 2% to about 25%.

4. The method of claim 1, comprising using a heterogeneous mixture comprising chitosans with different degrees of deacetylation.

5. The method of claim 1, comprising creating a drug releasing fiber comprising segments of chitosan with different degrees of deacetylation.

6. The method of claim 1, comprising creating a drug releasing fiber from chitosan and an extracellular matrix.

7. The method of claim 6, wherein the chitosan concentration is from about 0.5 wt. % to about 10 wt. %.

8. The method of claim 6, wherein said extracellular matrix comprises Matrigel.

9. The method of claim 6, wherein the extracellular matrix concentration is from about 1 vol. % to about 20 vol. %.

10. The method of claim 1, comprising coating said fiber with said extracellular matrix.

11. The method of claim 1, wherein a portion of said chitosan is sulfated chitosan.

12. The method of claim 1, wherein the sulfated chitosan concentration is from about 0.025 wt % to about 2 wt %.

13. A method of creating a drug releasing fiber from chitosan, said method comprising:
   a) obtaining a polymer solution comprising chitosan and a hydrochloric acid; and
   b) extruding the polymer solution into a coagulating bath comprising tris base.

14. The method of claim 13, wherein the concentration of the hydrochloric acid is about 1%.

15. The method of claim 13, wherein the concentration of tris base is between about 5% and about 15%.

16. The method of claim 13, is further comprising adding microspheres comprising at least one biomolecule to the chitosan solution prior to extruding.

17. The method of claim 16, wherein the biomolecule microsphere is made from a either a pure polymer, or is a copolymer or blend of the polymers selected from the group consisting of poly(L-lactic acid), poly(DL-lactic acid), poly (glycolic acid), polycaprolactone, and polyanhydridepoly (L-lactic acid).

18. The method of claim 13, further comprising applying at least one polymer coating comprising containing a biomolecule emulsion to said fibers thereby rendering said fibers capable of temporally controlling release of said multiple biomolecules, wherein said applying step is prior to the extruding step.

19. The method of claim 18, wherein said applying comprises passing said fiber through a spinneret comprising the emulsion.

20. The method of claim 13, further comprising assembling multiple fibers into a fabric, each wherein one or more fibers of said fabric comprising at least one biomolecule having a specific activity for a certain cell type, wherein said biomolecule may differ from the biomolecule in other fibers in said fabric.

21. The method of claim 20, wherein the fibers release the biomolecules over a period of time.

22. The method of claim 20, wherein at least a portion of the fibers may be coated to release various factors and chemicals over a period of time.

23. The method of claim 22, wherein a first portion of the coated fibers correspond to a first phase of dermal wound healing, a second portion of the coated fibers correspond to a second phase of dermal wound healing and a third portion of the coated fibers correspond to a third phase of dermal wound healing.

* * * * *